United States Patent
Bonutti et al.

(10) Patent No.: US 9,402,759 B2
(45) Date of Patent: Aug. 2, 2016

(54) CERVICAL TRACTION SYSTEMS AND METHOD

(71) Applicant: Bonutti Research, Inc., Effingham, IL (US)

(72) Inventors: Boris P. Bonutti, Effingham, IL (US); Glen A. Phillips, Effingham, IL (US); Henrik Bonutti, Bloomfield Hills, MI (US)

(73) Assignee: Bonutti Research, Inc., Effingham, IL (US)

(*) Notice: Subject to any disclaimer, the term of this patent is extended or adjusted under 35 U.S.C. 154(b) by 336 days.

(21) Appl. No.: 13/839,934

(22) Filed: Mar. 15, 2013

(65) Prior Publication Data
US 2014/0221895 A1 Aug. 7, 2014

Related U.S. Application Data

(60) Provisional application No. 61/761,040, filed on Feb. 5, 2013.

(51) Int. Cl.
  *A61F 5/04* (2006.01)
  *A61F 5/042* (2006.01)
  (Continued)

(52) U.S. Cl.
  CPC . *A61F 5/042* (2013.01); *A61F 5/04* (2013.01); *A61F 5/048* (2013.01); *A61H 1/02* (2013.01); *A61H 1/0218* (2013.01);
  (Continued)

(58) Field of Classification Search
  CPC .......... A61F 5/04; A61F 5/042; A61F 5/048; A61H 1/02; A61H 1/0218; A61H 1/0292; A61H 1/0296; A61H 2201/1609; A61H 2201/1611

USPC ............................................... 602/32, 36, 40
See application file for complete search history.

(56) References Cited

U.S. PATENT DOCUMENTS

| | | | |
|---|---|---|---|
| 432,327 | A | 7/1890 | Page |
| 433,227 | A | 7/1890 | Beacock |

(Continued)

FOREIGN PATENT DOCUMENTS

| | | |
|---|---|---|
| CA | 2066151 | 10/1992 |
| CA | 2065669 | 10/1993 |

(Continued)

OTHER PUBLICATIONS

Advertising materials from the Internet on Jun. 5, 1998 entitled: "Quadrant by Smith & Nephew DonJoy". "Entering a New Plane".

(Continued)

*Primary Examiner* — Keri J Nelson
(74) *Attorney, Agent, or Firm* — Senniger Powers LLP

(57) ABSTRACT

Embodiments may include a traction system, for example a cervical traction system for a neck of a user. Systems may include a housing assembly, plate assembly, handle assembly, and cable assembly. The housing assembly may include a drive assembly. The plate assembly may be operatively connected to the drive assembly. The handle assembly may be operatively connected to the drive assembly. The handle assembly may be configured to actuate movement of the plate assembly relative to the housing assembly. Embodiments may be configured to apply traction to the neck thereby providing a distraction distance or force to a portion of the cervical spine.

20 Claims, 41 Drawing Sheets

(51) Int. Cl.
*A61H 1/02* (2006.01)
*A61F 5/048* (2006.01)

(52) U.S. Cl.
CPC ............. *A61H 1/0296* (2013.01); *A61H 1/024* (2013.01); *A61H 1/0222* (2013.01); *A61H 1/0244* (2013.01); *A61H 1/0266* (2013.01); *A61H 1/0277* (2013.01); *A61H 1/0281* (2013.01); *A61H 1/0285* (2013.01); *A61H 1/0288* (2013.01); *A61H 1/0292* (2013.01); *A61H 2001/027* (2013.01); *A61H 2201/0157* (2013.01); *A61H 2201/1261* (2013.01); *A61H 2201/149* (2013.01); *A61H 2201/1609* (2013.01); *A61H 2201/1611* (2013.01); *A61H 2201/1635* (2013.01); *A61H 2201/1664* (2013.01); *A61H 2201/1676* (2013.01)

(56) References Cited

U.S. PATENT DOCUMENTS

| | | |
|---|---|---|
| 2,191,283 A | 2/1940 | Longfellow |
| 2,206,902 A | 7/1940 | Kost |
| 2,223,276 A | 11/1940 | Ward |
| 2,237,252 A | 4/1941 | Longfellow |
| 2,246,689 A | 6/1941 | Kost |
| 2,250,493 A | 7/1941 | Milne |
| 2,590,729 A | 3/1952 | Scognamillo |
| 2,590,739 A | 3/1952 | Wahner |
| 2,642,864 A | 6/1953 | Ward |
| 2,811,154 A | 10/1957 | Scholl |
| 2,820,455 A | 1/1958 | Hall |
| 2,829,562 A | 4/1958 | La Rue |
| 2,832,334 A | 4/1958 | Whitelaw |
| 3,083,708 A | 4/1963 | Gottfried |
| 3,338,237 A | 8/1967 | Sconce |
| 3,351,055 A | 11/1967 | Gottfried |
| 3,548,818 A | 12/1970 | Kaplan |
| 3,580,248 A | 5/1971 | Larson |
| 3,673,620 A | 7/1972 | Saunders |
| 3,675,646 A | 7/1972 | Corcoran |
| 3,698,389 A | 10/1972 | Guedel |
| 3,701,349 A | 10/1972 | Larson |
| 3,724,452 A | 4/1973 | Nitschke |
| 3,760,056 A | 9/1973 | Rudy |
| 3,795,243 A | 3/1974 | Miller |
| 3,811,434 A | 5/1974 | Jacobson |
| 3,814,419 A | 6/1974 | Bjorklund |
| 3,856,004 A | 12/1974 | Cox |
| 3,915,161 A | 10/1975 | Shields |
| 3,955,565 A | 5/1976 | Johnson, Jr. |
| 3,970,316 A | 7/1976 | Westmoreland |
| 3,976,057 A | 8/1976 | Barclay |
| 4,015,597 A | 4/1977 | Beaver |
| 4,039,183 A | 8/1977 | Sakurada |
| 4,076,022 A | 2/1978 | Walker |
| 4,084,267 A | 4/1978 | Zadina |
| 4,108,170 A | 8/1978 | Spann |
| 4,180,870 A | 1/1980 | Radulovic |
| 4,214,577 A | 7/1980 | Hoy |
| 4,229,001 A | 10/1980 | Roman |
| 4,237,873 A | 12/1980 | Terry |
| 4,241,731 A | 12/1980 | Pauley |
| 4,273,113 A | 6/1981 | Hofstein |
| 4,285,773 A | 8/1981 | Taciuk |
| 4,320,748 A | 3/1982 | Racette |
| 4,321,718 A * | 3/1982 | Chern .................. A47D 15/003 297/391 |
| 4,363,481 A | 12/1982 | Erickson |
| 4,370,977 A | 2/1983 | Mauldin |
| 4,383,523 A | 5/1983 | Schurman |
| 4,396,013 A | 8/1983 | Hasslinger |
| 4,401,111 A | 8/1983 | Blackstone |
| 4,417,569 A | 11/1983 | Brudny |
| 4,441,489 A | 4/1984 | Evans |
| 4,454,871 A | 6/1984 | Mann |
| 4,456,001 A | 6/1984 | Pescatore |
| 4,456,002 A | 6/1984 | Barber |
| 4,502,470 A | 3/1985 | Kiser |
| 4,502,681 A | 3/1985 | Blomqvist |
| 4,508,109 A | 4/1985 | Saunders |
| 4,508,111 A | 4/1985 | Hepburn |
| 4,509,509 A | 4/1985 | Bouvet |
| 4,538,595 A | 9/1985 | Hajianpour |
| 4,538,600 A | 9/1985 | Hepbrun |
| 4,545,572 A | 10/1985 | Day |
| 4,570,619 A | 2/1986 | Gamm |
| 4,576,151 A | 3/1986 | Carmichael |
| 4,583,532 A * | 4/1986 | Jones .............................. 602/32 |
| 4,589,406 A | 5/1986 | Florek |
| 4,606,542 A | 8/1986 | Segal |
| 4,612,919 A | 9/1986 | Best |
| 4,628,913 A | 12/1986 | Lerman |
| 4,641,639 A | 2/1987 | Padilla |
| 4,653,479 A | 3/1987 | Maurer |
| 4,665,905 A | 5/1987 | Brown |
| 4,693,239 A | 9/1987 | Clover, Jr. |
| 4,716,889 A | 1/1988 | Saringer |
| 4,718,665 A | 1/1988 | Airy |
| 4,727,865 A | 3/1988 | Hill-Byrne |
| 4,739,334 A | 4/1988 | Soref |
| 4,765,320 A | 8/1988 | Lindemann |
| 4,771,493 A | 9/1988 | Park |
| 4,788,941 A | 12/1988 | Villeneuve |
| 4,790,301 A | 12/1988 | Silfverskiold |
| 4,793,334 A | 12/1988 | McGuinness |
| 4,805,601 A | 2/1989 | Eischen, Sr. |
| 4,807,601 A | 2/1989 | Wright |
| 4,809,688 A | 3/1989 | Aymerica del Valle |
| 4,834,073 A | 5/1989 | Bledsoe |
| 4,844,094 A | 7/1989 | Grim |
| 4,844,454 A | 7/1989 | Rogers |
| 4,844,455 A | 7/1989 | Funkhouser, Jr. |
| 4,848,326 A | 7/1989 | Lonardo |
| 4,862,877 A | 9/1989 | Barber |
| 4,865,024 A | 9/1989 | Hensley |
| 4,869,267 A | 9/1989 | Grim |
| 4,869,499 A | 9/1989 | Schiraldo |
| 4,884,454 A | 12/1989 | Johnson |
| 4,913,135 A | 4/1990 | Mattingly |
| 4,913,755 A | 4/1990 | Grim |
| 4,930,497 A | 6/1990 | Saringer |
| 4,953,543 A | 9/1990 | Grim |
| 4,955,369 A | 9/1990 | Bledsoe |
| 4,955,396 A | 9/1990 | Fralick |
| 4,957,281 A | 9/1990 | Christolear, Jr. |
| 4,964,402 A | 10/1990 | Grim |
| 4,991,234 A | 2/1991 | Greenberg |
| 4,996,979 A | 3/1991 | Grim |
| 5,005,563 A | 4/1991 | Veale |
| 5,018,514 A | 5/1991 | Grood |
| 5,019,050 A | 5/1991 | Lynn |
| 5,025,782 A | 6/1991 | Salerno |
| 5,027,688 A | 7/1991 | Suzuki |
| 5,027,801 A | 7/1991 | Grim |
| 5,027,802 A | 7/1991 | Donohue |
| 5,036,837 A | 8/1991 | Mitchell |
| 5,036,838 A | 8/1991 | Sherman |
| 5,052,375 A | 10/1991 | Stark |
| 5,070,866 A | 12/1991 | Alexander |
| 5,078,128 A | 1/1992 | Grim |
| 5,088,481 A | 2/1992 | Darby |
| 5,100,403 A | 3/1992 | Hotchkiss |
| 5,102,411 A | 4/1992 | Hotchkiss |
| 5,116,359 A | 5/1992 | Moore |
| 5,125,400 A | 6/1992 | Johnson, Jr. |
| 5,135,470 A | 8/1992 | Reeves |
| 5,139,475 A | 8/1992 | Robicsek |
| 5,141,489 A | 8/1992 | Sereboff |
| 5,154,186 A | 10/1992 | Laurin |
| 5,156,589 A | 10/1992 | Langen |
| 5,163,451 A | 11/1992 | Grellas |
| 5,167,612 A | 12/1992 | Bonutti |
| 5,171,296 A | 12/1992 | Herman |

(56) References Cited

U.S. PATENT DOCUMENTS

| | | |
|---|---|---|
| 5,191,903 A | 3/1993 | Donohue |
| 5,197,942 A | 3/1993 | Brady |
| 5,201,702 A | 4/1993 | Mars |
| 5,201,772 A | 4/1993 | Maxwell |
| 5,203,321 A | 4/1993 | Donovan |
| 5,205,813 A | 4/1993 | Schmidt |
| 5,211,161 A | 5/1993 | Stef |
| 5,213,094 A | 5/1993 | Bonutti |
| 5,213,095 A | 5/1993 | Dague |
| 5,218,954 A | 6/1993 | van Bemmelen |
| 5,226,245 A | 7/1993 | Lamont |
| 5,232,435 A | 8/1993 | Leibinsohn |
| 5,252,101 A | 10/1993 | Rosenwinel |
| 5,252,102 A | 10/1993 | Singer |
| 5,261,125 A | 11/1993 | Cartwright |
| 5,265,625 A | 11/1993 | Bodman |
| 5,277,695 A | 1/1994 | Johnson, Jr. |
| 5,285,773 A | 2/1994 | Bonutti |
| 5,297,540 A | 3/1994 | Kaiser |
| 5,312,322 A | 5/1994 | Santana |
| 5,316,022 A | 5/1994 | Schiek, Sr. |
| 5,323,435 A | 6/1994 | Baversten |
| RE34,661 E | 7/1994 | Grim |
| 5,327,882 A | 7/1994 | Saringer |
| 5,328,448 A | 7/1994 | Gray, Sr. |
| 5,329,705 A | 7/1994 | Grim |
| 5,348,530 A | 9/1994 | Grim |
| 5,349,956 A | 9/1994 | Bonutti |
| 5,352,216 A | 10/1994 | Shiono |
| 5,354,260 A | 10/1994 | Cook |
| 5,364,323 A | 11/1994 | Liu |
| 5,365,947 A | 11/1994 | Bonutti |
| 5,370,133 A | 12/1994 | Darby |
| 5,372,597 A | 12/1994 | Hotchkiss |
| 5,376,091 A | 12/1994 | Hotchkiss |
| 5,378,223 A | 1/1995 | Grim |
| 5,382,226 A | 1/1995 | Graham |
| 5,385,536 A | 1/1995 | Burkhead |
| 5,389,065 A | 2/1995 | Johnson, Jr. |
| 5,391,132 A | 2/1995 | Greenwald |
| 5,395,303 A | 3/1995 | Bonutti |
| 5,399,152 A | 3/1995 | Habermeyer |
| 5,403,265 A | 4/1995 | Berguer |
| 5,407,420 A | 4/1995 | Bastyr |
| 5,407,422 A | 4/1995 | Matthijs |
| 5,417,643 A | 5/1995 | Taylor |
| 5,419,757 A | 5/1995 | Daneshvar |
| 5,421,874 A | 6/1995 | Pearce |
| 5,435,009 A | 7/1995 | Schild |
| 5,437,611 A | 8/1995 | Stern |
| 5,452,205 A | 9/1995 | Telepko |
| 5,453,075 A | 9/1995 | Bonutti |
| 5,453,082 A | 9/1995 | Lamont |
| 5,456,268 A | 10/1995 | Bonutti |
| 5,456,286 A | 10/1995 | Warner |
| 5,464,385 A | 11/1995 | Grim |
| 5,466,213 A | 11/1995 | Hogan |
| 5,466,250 A | 11/1995 | Johnson, Jr. |
| 5,472,407 A | 12/1995 | Schenck |
| 5,492,133 A | 2/1996 | NcVickar |
| 5,503,619 A | 4/1996 | Bonutti |
| 5,503,622 A | 4/1996 | Wehr |
| 5,503,908 A | 4/1996 | Faass |
| 5,518,009 A | 5/1996 | Ruiz-Gonzalez |
| 5,520,181 A | 5/1996 | Kreidler |
| 5,520,628 A | 5/1996 | Wehr |
| 5,527,269 A | 6/1996 | Reithofer |
| 5,531,669 A | 7/1996 | Varnau |
| 5,535,274 A | 7/1996 | Braitberg |
| 5,538,486 A | 7/1996 | France |
| 5,569,175 A | 10/1996 | Chitwood |
| 5,571,077 A | 11/1996 | Klearman |
| 5,577,998 A | 11/1996 | Johnson, Jr. |
| 5,605,535 A | 2/1997 | Lepage |
| 5,609,570 A | 3/1997 | Lamont |
| 5,611,764 A | 3/1997 | Bonutti |
| 5,620,411 A | 4/1997 | Schumann |
| 5,626,537 A | 5/1997 | Danyo |
| 5,647,378 A | 7/1997 | Farnum |
| 5,653,680 A | 8/1997 | Cruz |
| 5,665,059 A | 9/1997 | Klearman |
| 5,681,269 A | 10/1997 | Basaj |
| 5,685,830 A | 11/1997 | Bonutti |
| 5,697,894 A | 12/1997 | Guillichsen |
| 5,713,841 A | 2/1998 | Graham |
| 5,755,679 A | 5/1998 | Selner |
| 5,761,834 A | 6/1998 | Grim |
| 5,772,619 A | 6/1998 | Corbett |
| 5,778,565 A | 7/1998 | Holt |
| 5,788,659 A | 8/1998 | Haas |
| 5,792,084 A | 8/1998 | Wilson |
| 5,820,577 A | 10/1998 | Taylor |
| 5,823,975 A | 10/1998 | Stark |
| 5,833,639 A | 11/1998 | Nunes |
| 5,839,139 A | 11/1998 | Fink |
| 5,848,979 A | 12/1998 | Bonutti |
| 5,848,984 A * | 12/1998 | Bachar ............... A61F 5/01 602/32 |
| 5,865,773 A | 2/1999 | Koledin |
| 5,868,471 A | 2/1999 | Graham |
| 5,882,320 A | 3/1999 | Peterson |
| 5,882,323 A | 3/1999 | Belkin |
| 5,919,148 A | 7/1999 | Marko |
| 5,929,782 A | 7/1999 | Stark |
| 5,940,992 A | 8/1999 | Darby |
| 5,943,705 A | 8/1999 | Sink |
| 5,951,499 A | 9/1999 | Saringer |
| 5,957,876 A | 9/1999 | D'Amico |
| 5,980,435 A | 11/1999 | Joutras |
| 6,007,500 A | 12/1999 | Quintinskie, Jr. |
| 6,021,780 A | 2/2000 | Darby |
| 6,027,468 A | 2/2000 | Pick |
| 6,045,522 A | 4/2000 | Grober |
| 6,050,965 A | 4/2000 | Pillai |
| 6,053,169 A | 4/2000 | Hunt |
| 6,059,548 A | 5/2000 | Campbell |
| 6,059,576 A | 5/2000 | Brann |
| 6,076,266 A | 6/2000 | Beckingham |
| 6,093,162 A | 7/2000 | Fairleigh |
| 6,099,489 A | 8/2000 | Herzberg |
| 6,113,562 A | 9/2000 | Bonutti |
| 6,142,964 A | 11/2000 | Gilmour |
| 6,142,965 A | 11/2000 | Matthewson |
| 6,155,994 A | 12/2000 | Hubbard |
| 6,171,273 B1 | 1/2001 | Saunders |
| 6,179,747 B1 | 1/2001 | Kelley |
| 6,179,800 B1 | 1/2001 | Torrens |
| 6,184,797 B1 | 2/2001 | Stark |
| 6,196,956 B1 | 3/2001 | Brown |
| 6,228,044 B1 | 5/2001 | Jensen |
| 6,267,742 B1 | 7/2001 | Krivosha |
| 6,296,595 B1 | 10/2001 | Stark |
| 6,305,749 B1 | 10/2001 | O'Connor |
| 6,371,123 B1 | 4/2002 | Stark |
| 6,384,755 B1 | 5/2002 | Hayden |
| 6,409,691 B1 | 6/2002 | Dakin |
| 6,436,058 B1 | 8/2002 | Krahner |
| 6,468,240 B1 | 10/2002 | Saunders |
| 6,485,447 B1 | 11/2002 | Lavery |
| 6,491,694 B1 | 12/2002 | Orsak |
| 6,502,577 B1 | 1/2003 | Bonutti |
| 6,503,213 B2 | 1/2003 | Bonutti |
| 6,506,172 B1 | 1/2003 | Hepburn |
| 6,506,174 B1 | 1/2003 | Saunders |
| 6,509,659 B1 | 1/2003 | Carroll |
| 6,572,571 B2 | 6/2003 | Lowe |
| 6,575,926 B2 | 6/2003 | Bonutti |
| 6,599,255 B2 | 7/2003 | Zhang |
| 6,599,263 B1 | 7/2003 | Bonutti |
| 6,637,429 B2 | 10/2003 | Mundrick |
| 6,682,497 B2 | 1/2004 | Jensen |
| 6,743,187 B2 | 6/2004 | Solomon |
| 6,770,047 B2 | 8/2004 | Bonutti |
| 6,890,285 B2 | 5/2005 | Rahman |

(56) References Cited

U.S. PATENT DOCUMENTS

| | | |
|---|---|---|
| 6,899,690 B2 | 5/2005 | Saunders |
| 6,921,377 B2 | 7/2005 | Bonutti |
| 6,929,616 B2 | 8/2005 | Bonutti |
| 6,945,986 B2 * | 9/2005 | Lope .................. 606/240 |
| 6,958,048 B2 | 10/2005 | Bonutti |
| 6,971,997 B1 | 12/2005 | Ryan |
| 6,974,431 B2 | 12/2005 | Jensen |
| 7,101,347 B2 | 9/2006 | Culhane |
| 7,108,671 B2 | 9/2006 | Saunders |
| 7,112,179 B2 | 9/2006 | Bonutti |
| 7,182,738 B2 | 2/2007 | Bonutti |
| 7,189,214 B1 | 3/2007 | Saunders |
| 7,204,814 B2 | 4/2007 | Peles |
| 7,306,573 B2 | 12/2007 | Bonutti |
| 7,347,834 B2 * | 3/2008 | Han .................. 602/32 |
| 7,404,804 B2 | 7/2008 | Bonutti |
| 7,566,314 B2 | 7/2009 | Saunders |
| 7,654,974 B2 * | 2/2010 | Bass .................. 602/32 |
| 2001/0047209 A1 | 11/2001 | Solomon |
| 2002/0029784 A1 | 3/2002 | Stark |
| 2002/0183655 A1 | 12/2002 | Zhang |
| 2003/0120183 A1 | 6/2003 | Simmons |
| 2004/0153010 A1 | 8/2004 | Bonutti |
| 2004/0215120 A1 | 10/2004 | Jensen |
| 2005/0010152 A1 | 1/2005 | Becerra |
| 2006/0036205 A1 | 2/2006 | Bonutti |
| 2006/0217647 A1 | 9/2006 | Rogachevsky |
| 2007/0038161 A1 | 2/2007 | Bonutti |
| 2007/0055190 A1 | 3/2007 | Bonutti |
| 2007/0100267 A1 | 5/2007 | Bonutti |
| 2007/0135738 A1 | 6/2007 | Bonutti |
| 2007/0197605 A1 | 8/2007 | Glombik |
| 2007/0219475 A1 | 9/2007 | Bonutti |
| 2007/0219476 A1 | 9/2007 | Bonutti |
| 2008/0091132 A1 | 4/2008 | Bonutti |

FOREIGN PATENT DOCUMENTS

| | | |
|---|---|---|
| DE | 405327 | 10/1924 |
| DE | 2829562 | 1/1980 |
| DE | 8806231.7 U1 | 5/1988 |
| EP | 0181668 | 5/1986 |
| EP | 0181688 | 5/1986 |
| EP | 0380060 | 1/1990 |
| EP | 0510840 | 10/1992 |
| FR | 2661333 | 4/1992 |
| JP | 4261657 | 9/1992 |
| JP | 2000187113 A | 7/2000 |
| JP | 2001087296 | 4/2001 |
| JP | 2001087296 A | 4/2001 |
| SU | 1158195 A1 | 5/1985 |
| SU | 1426580 A1 | 9/1988 |
| SU | 1671296 A1 | 8/1991 |
| WO | 8804543 | 6/1988 |
| WO | 2004073143 | 1/2004 |
| WO | 2005086741 | 9/2005 |
| WO | 2007051168 | 5/2007 |
| WO | 2007109638 | 9/2007 |
| WO | 2008036895 | 8/2008 |

OTHER PUBLICATIONS

Advertising materials from the Internet on Jun. 5, 1998 entitled: "Make DonJoy's Quadrant Your First Choice for Effective Post-Operative Shoulder Treatment". "Quadrant Brace Specifications".

Advertising materials from the Internet on Jun. 5, 1998 entitled: "UltraslingTM by DonJoy".

Neporent et al. "Weight Training for Dummies" 1997, p. 294.

Dynasplint Systems Inc. "Practitioner Information for Dynasplint LPS Orthosis—Knee Extension". Date known but prior to Aug. 23, 1991.

Publication by UE Tech. Technology Meeting Human Needs. Rehabilitation Product Catalog. vol. 7. publication dale unknown but prior to Oct. 13, 1998.

Taber's Cyclopedic Medical Dictionary 16th Edition (1989) (#34). p. 521. definition of "distraction".

Joint Active Sytems. Inc .. JAS; The Proven Approach to Restoring ROM (online). Copyright 2004 www.jointactivesystems.com.

International Preliminary Report for PCT/US2014/014765, dated Aug. 20, 2015.

* cited by examiner

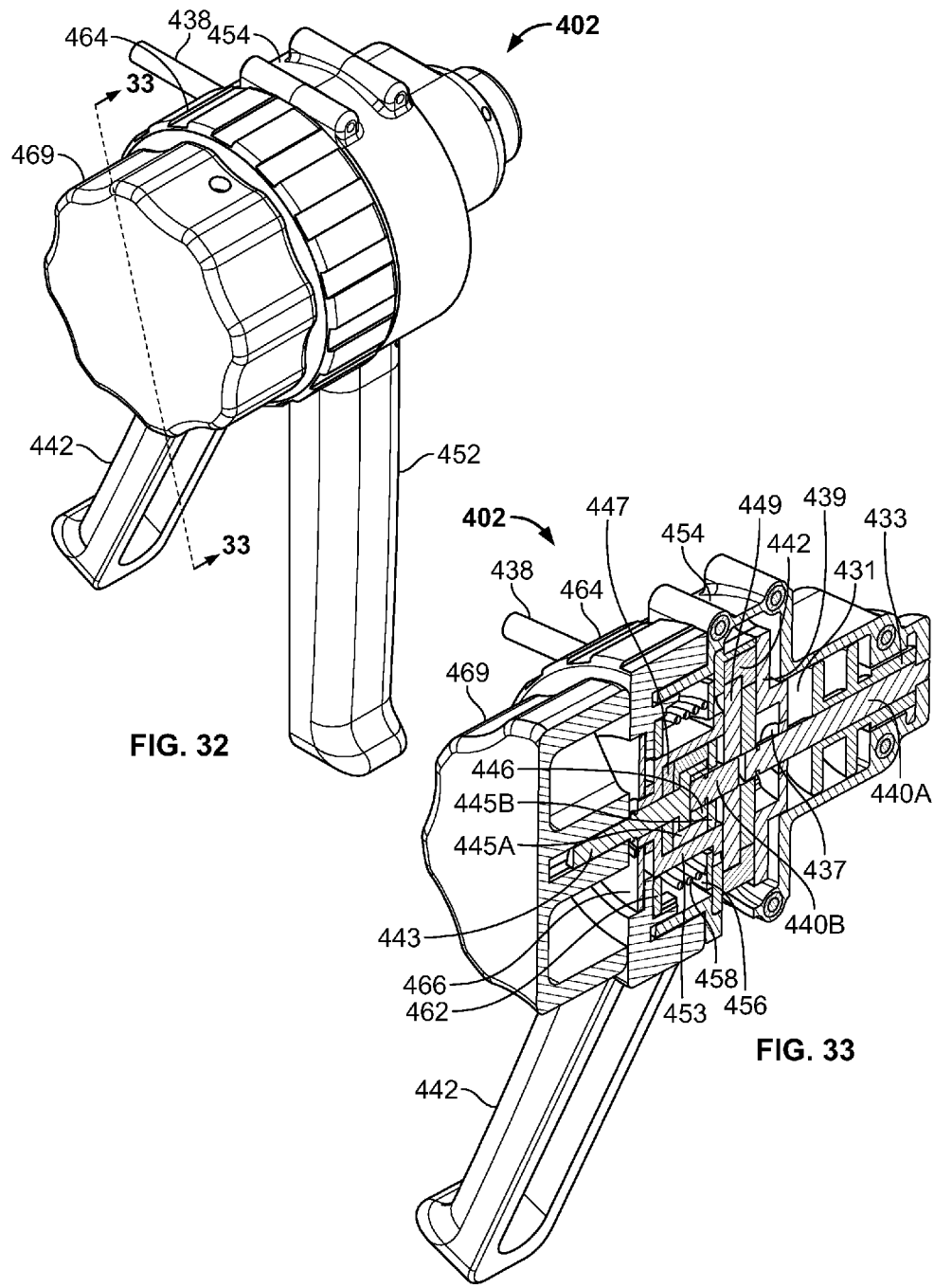

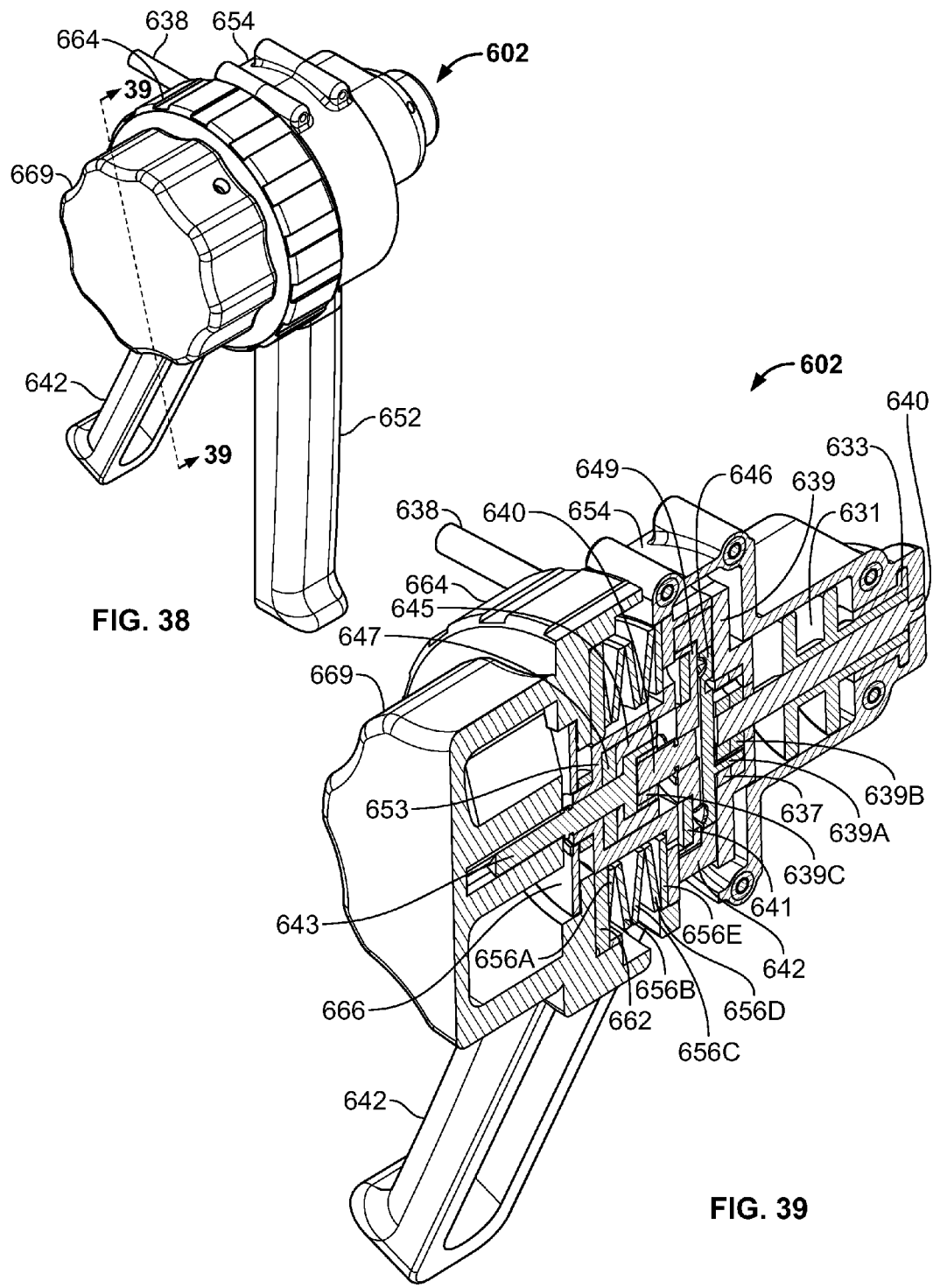

CERVICAL TRACTION SYSTEMS AND METHOD

CROSS-REFERENCE TO RELATED APPLICATIONS

This non-provisional application is based on and claims priority to U.S. Provisional Application No. 61/761,040 filed Feb. 5, 2013, titled "CERVICAL TRACTION DEVICES AND METHOD", the entire contents of which are hereby incorporated by reference in its entirety as if set forth fully herein.

FIELD

Embodiments of the present disclosure relate to devices and methods, for example, configured to provide traction and/or distraction. Further embodiments may be configured for any portion of the body, for example the spine. Additional embodiments may be configured for the cervical spine, for example to provide cervical traction and/or distraction. Embodiments may be configured to adjust and/or control a distraction distance, force, and/or angle.

BACKGROUND

Typically, the spine is under continuous loading, for example loading of the spinous processes of the vertebral bodies, the facet, and the discs. The cervical spine may be loaded by the weight of the head, by gravity, or sometimes simply by carrying objects with the upper extremities. In addition, the load changes whether the vertebra is flexed forward or extended backward. When the vertebra is flexed forward, there may be an increased load on the disc and the anterior element. When the vertebra is extended posteriorly, there may be an increased load across the facet joints. As such, it may be beneficial to unload the vertebra, especially of the cervical spine.

Traditional traction devices and methods primarily rely on a pneumatic drive assembly for distraction. Pneumatic traction devices may include a carriage that moves relative to a support structure when pressurized. A user may operate a hand pump that is fluidly connected to the pneumatic drive assembly to inject pressurized air. The hand pump injects pressure into the pneumatic traction device thereby moving the carriage a variable distance. A pressure relief mechanism may be operated by the user to release pressure from the pneumatic traction device. Pneumatic devices may suffer from air pressure loss during use, difficulty with use of the hand pump, uncontrollable and impulsive traction release, non-adjustable traction angles and support features, and expensive and bulky pneumatic components.

More specifically, these pneumatic devices are driven by imprecise volumetric or pressure changes in fluids, not interaction between solid mechanical components. For example, volumetric or pressure changes may result in an applied pressure, which may not directly translate into a precise distraction distance, force, and/or angle with respect to portions of the body. Also, pneumatic devices may employ measurement gauges reflecting volume or pressure but may not provide a precise mechanism to indicate or control the distraction distance, for example in terms of millimeters. Moreover, pneumatic devices are unable to maintain a set distraction distance, because pneumatic pressure is gradually lost due to fluid compression or leakage throughout the pneumatic system. For precise distraction, cervical traction devices may control and maintain distraction to a precise distance, which may not be possible for a pneumatically driven system. Although volumetric or pressure changes may be an indicator of the pressure on the pneumatic device itself, reliance on volume or pressure changes may not translate to a repeatable and precise distraction distance, force, and/or angle necessary for effective treatment.

In addition, the atmospheric conditions may cause variations in traditional pneumatic devices. Depending on whether the temperature is colder or warmer, the pressure applied and measured may change. If humidity increases or decreases, the applied pressure may be different, for example based on the material characteristics of the pneumatic fluid or the body. Even at different altitudes, the atmospheric pressure may vary thereby inducing inaccuracy in devices relying on pressure. With any of these changes, pneumatic devices may apply and measure pressure with substantially varying accuracy. Pneumatic drive devices may be affected by environmental conditions (i.e. temperature, humidity, and altitude) that may only have a negligible effect on mechanical drive devices. Pneumatic devices may not be able to provide and maintain the precise and consistent distraction distances or forces that mechanical devices may provide. Also, considering the relevance of the distraction distance in treating conditions of the spine, pneumatic devices may be imprecise when compared to a device with measurable and controllable distraction distances.

There exists a need for traction devices and methods configured to provide ease of use, precise distraction forces and distances, adjustable traction angles and support components, controlled traction application and release, and reduction in unnecessary components.

SUMMARY

Embodiments may include a traction system, for example a cervical traction system for a neck of a patient or user. Systems may include a housing assembly, plate assembly, handle assembly, and/or cable assembly. The housing assembly may include a drive assembly. The plate assembly may be operatively connected to the drive assembly. The handle assembly operatively connected to the drive assembly. The handle assembly may be configured to actuate movement of the plate assembly relative to the housing assembly. This may apply traction to the neck thereby providing a distraction distance, force, and/or angle to portions of the spine.

Further embodiments may include a housing assembly, plate assembly, handle assembly, and cable assembly. The plate assembly may include first and second supports configured to engage a portion of a head and/or neck of a patient or user. The plate assembly may include a transverse drive member configured to adjust a transverse distance between the first and second supports. The housing assembly may include a drive assembly configured to longitudinally move the plate assembly relative to the housing assembly. The handle assembly may be operatively connected to the drive assembly. Movement of the plate assembly by the drive assembly may urge the first and second supports against the head and/or neck to apply a distraction distance, force, and/or angle to the cervical spine. The handle assembly, housing assembly, and/or drive assembly may include traction limiting and/or anti-reversing features, for example, to control the distraction distance or force.

Embodiments may also include methods of using a traction device, for example a cervical traction device for a neck of a patient. Methods may comprise providing the cervical traction system including a housing assembly having a longitudinal drive, a plate assembly having a transverse drive, and a handle assembly. Methods may include adjusting the traction angle of the housing assembly, adjusting supports in transverse and/or angular directions, adjusting or setting a limit knob, urging the plate assembly to a longitudinal distance based on the height of the patient, positioning the neck and/or head of a patient with respect to the plate assembly, actuating a traction knob or a trigger of the handle assembly to advance the longitudinal drive member, and/or releasing the plate assembly with a release on the handle assembly, housing assembly, or drive assembly. The longitudinal drive may be configured to move the plate assembly relative to the housing assembly to provide a controlled distraction distance, force, and/or angle to at least a portion of the neck and/or cervical spine.

Additional embodiments of the present application are disclosed herein including the accompanying drawings.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein:

FIG. 32 illustrates an isometric view of an embodiment, for example an alternative handle assembly;

FIG. 33 illustrates a section view of an embodiment of FIG. 32;

FIG. 38 illustrates an isometric view of an embodiment, for example an alternative handle assembly;

FIG. 39 illustrates a section view of an embodiment of FIG. 38;

DETAILED DESCRIPTION

Figure 1:
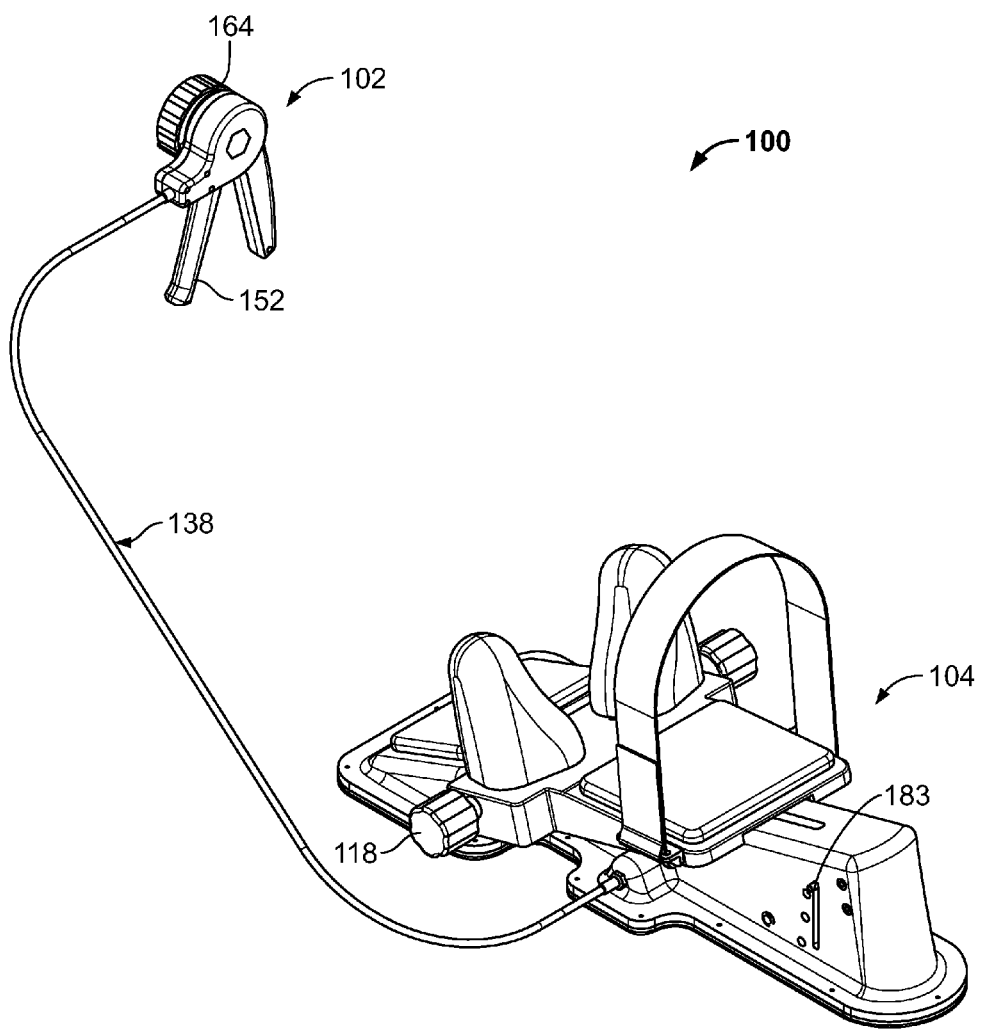
FIG. 1 illustrates an isometric view of an embodiment of the present disclosure, for example, including a traction system.
Figure 2:
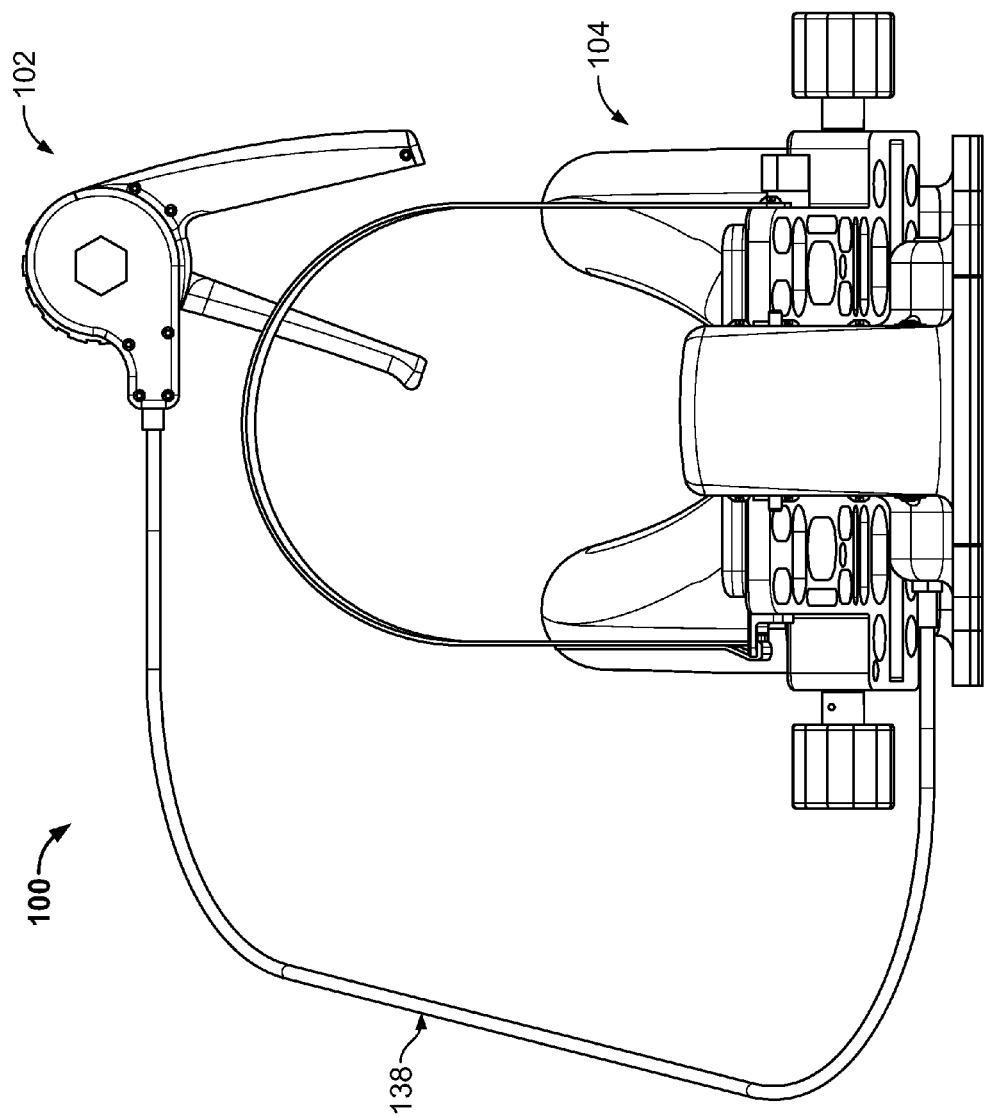
FIG. 2 illustrates a rear view of an embodiment of FIG. 1.
Figure 3:
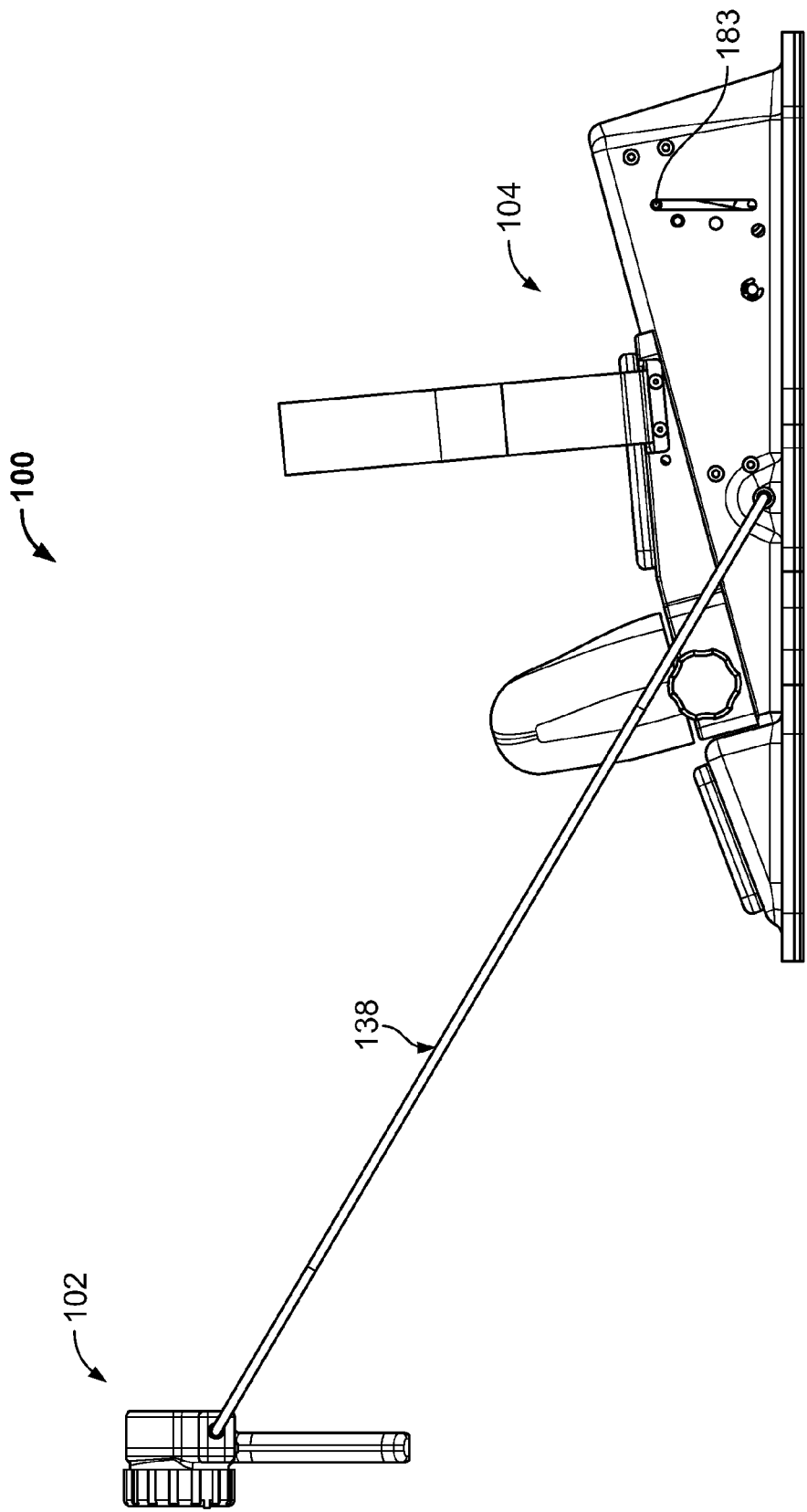
FIG. 3 illustrates a side view of an embodiment of FIG. 1.

Embodiments of the present disclosure are configured to provide a distraction distance, force, and/or angle to reduce a load of a spine, for example a cervical spine. The spine may be unloaded by distraction of a disc space, facets, vertebral body, or any other portion of the spine. For example, embodiments herein may be configured to apply a force that may distract portions of the spine, for example, to decrease the loading of gravity or weight across the vertebra of the cervical spine. Embodiments may also be configured to treat the thoracic and lumbar spine. With application of a force to distract the spine, the forces across the spine may decrease. The fraction devices and methods herein may be configured to neutralize spinal loading and/or distract a portion of the spine. Embodiments may be configured to control, adjust, or limit a distraction distance, force, and/or angle on the spine.

The spine may also be loaded in non-neutral positions. For example, if the vertebra is flexed forward or extended backward, the discs of the spine may be loaded. If the spine is in a neutral or slightly extended position, the load across the spine (i.e. facets) may be decreased. Flexion, extension, and/or rotation may also allow for decreased loading across certain portions of the spine. For example, if the vertebra is extended, the load decreases across the vertebral disc spaces. If the spine is distracted and extended, the load across the disc space would further decrease. If the vertebra is loaded in neutral to slight flexion, this may decrease the load across the posterior elements of the facet joints. If a distraction force is applied while controlling rotation, it may decrease the load across the spine, for example across both facet joints and the disc. Embodiments may be configured to provide a traction distance, force, and/or angle configured to unload a specific condition of the spine.

Unloading and/or distraction of the spine may be especially relevant to numerous medical conditions, for example spondylosis. Spondylosis is a condition in which the facets develop arthritic hypertrophy of the facets. The facets may pinch a nerve root and the disc space may lose vertebral disc space height due to loss of proteoglycans and fluids in the proteoglycans. By distracting the spine, water may imbibe into the vertebral disc space. Also, distraction may unload nerve roots, vertebral endplate, disc space, anterior posterior longitudinal ligament, ligamentum flavum, and any other portion of the spine. Distraction may also decrease pressure on the nerves to decrease pain and/or nerve entrapment. Distraction of the spine may relieve some medical conditions.

The traction systems and devices herein may be configured to distract the spine, unload the spinal elements, and/or decrease the load from gravity and daily activities. This may be accomplished by decreasing the load or by additionally distracting the spine. Distraction may relieve the load, pain, and/or nerve fibers, for example by creating greater space and/or reducing compression. Distraction may unload the disc space, facet joint, ligamentum flavum, or any other portion of the spine. Although the traction systems herein may provide traction by moving, pulling, or pushing components of the traction system relative to portions of the body, this may result in a decrease in loads of the spine and/or distraction of cervical spine at one or multiple locations.

Devices and methods herein may be configured to provide traction to distract a portion of a body, for example a neck including a cervical spine of a body. For the purposes of the present application, distraction may include, for example, the application of distance or force to or the movement, stabilization, unloading, or separation of any portion of the body. Traction may include pushing, pulling, or movement along a distance, for example, to distract a portion of the spine. Embodiments may be configured to treat any portion of the body, for example a neck, a spine, a back, a knee, a hip, a finger, a toe, a wrist, an ankle, an elbow, a shoulder, or any other body portion disclosed herein. Embodiments may be configured to provide traction to any portion of the spine, for example one or more transverse process, pedicle, facet, spinous process, posterior arch, odontoid process, posterior tubercle, lateral articular process, uncinate process, anterior tubercle, carotid tubercle, lamina, and/or vertebral body. The devices and methods herein may include an orthosis and/or be configured to correct any musculoskeletal disorder or condition of the body.

Embodiments of the present disclosure may include a fraction system including a handle assembly, cable assembly, housing assembly, drive assembly, and/or a plate assembly. The cable assembly may operatively connect the handle assembly and drive assembly. The drive assembly may be operatively connected to the plate assembly. A force actuated by a user may be translated to and/or through the handle assembly, cable assembly, drive assembly, and/or plate assembly to move the plate assembly relative to the housing assembly. Movement of the plate assembly relative to the housing assembly may provide a distraction distance and/or force to at least a portion of a body, for example the cervical vertebra of the spine.

In use, the housing assembly may be positioned on any support surface, for example a ground, floor, bed, or table. The slope or traction angle of the housing assembly may be adjusted, for example, by depressing the adjustment buttons on the housing assembly. The magnitude of distraction distance and/or force to be applied to the user may be adjusted by rotating a traction limit knob of the handle assembly, for example, including a clutch configured to disengage at the set traction limit. Also, the position of the supports of the head and/or neck may be adjusted by rotating one or both support knobs, for example to adjust transverse separation and/or rotational position of the supports to receive the neck and/or head of the user. Rotation may be about the axis of the supports and/or about an axis parallel to the transverse adjustment. The user may then position the neck and/or head between the supports with the back of the user's head adjacent the pad of the plate assembly and the base of the user's neck adjacent the pad of the housing assembly.

After the user is positioned, the position of the supports may be transversely and/or rotationally adjusted to contact the neck and/or base of the head, for example near the mastoid processes at the base of the skull. Also, the plate assembly may be longitudinally released and/or adjusted with a release in the handle assembly, housing assembly, or drive assembly, for example to provide longitudinal adjustment of the plate assembly. The user may then pull the trigger and/or rotate a knob of the handle assembly to actuate movement of the plate assembly along the housing assembly. In addition, the handle assembly may include both a trigger and a knob, each providing a different rate of movement between the plate assembly and housing assembly. For example, the trigger may be configured to provide finer or more graduated movement than the knob, or vice versa. After actuation of the plate assembly, the supports apply a force to the head relative to the base of the neck, thereby applying fraction to distract the vertebra of the cervical spine. The size, dimensions, and/or adjustments of the traction system may be configured to provide a distraction distance or force, which may be controlled by the set traction limit.

The handle assembly may longitudinally and/or rotationally translate a force from the handle assembly to the drive assembly, for example by increasing or decreasing tension or rotation of a cable or flexible shaft. The drive assembly may apply a force to the plate assembly, for example with a lever, worm gear, ratchet, slotted plate, and/or by pulling or pushing the plate assembly. The drive assembly may then move the plate assembly thereby advancing the plate assembly along the housing assembly. Actuation of the handle assembly ultimately translates a force to the plate assembly, thereby controllably applying a distraction distance or force to the spine.

Figure 4:
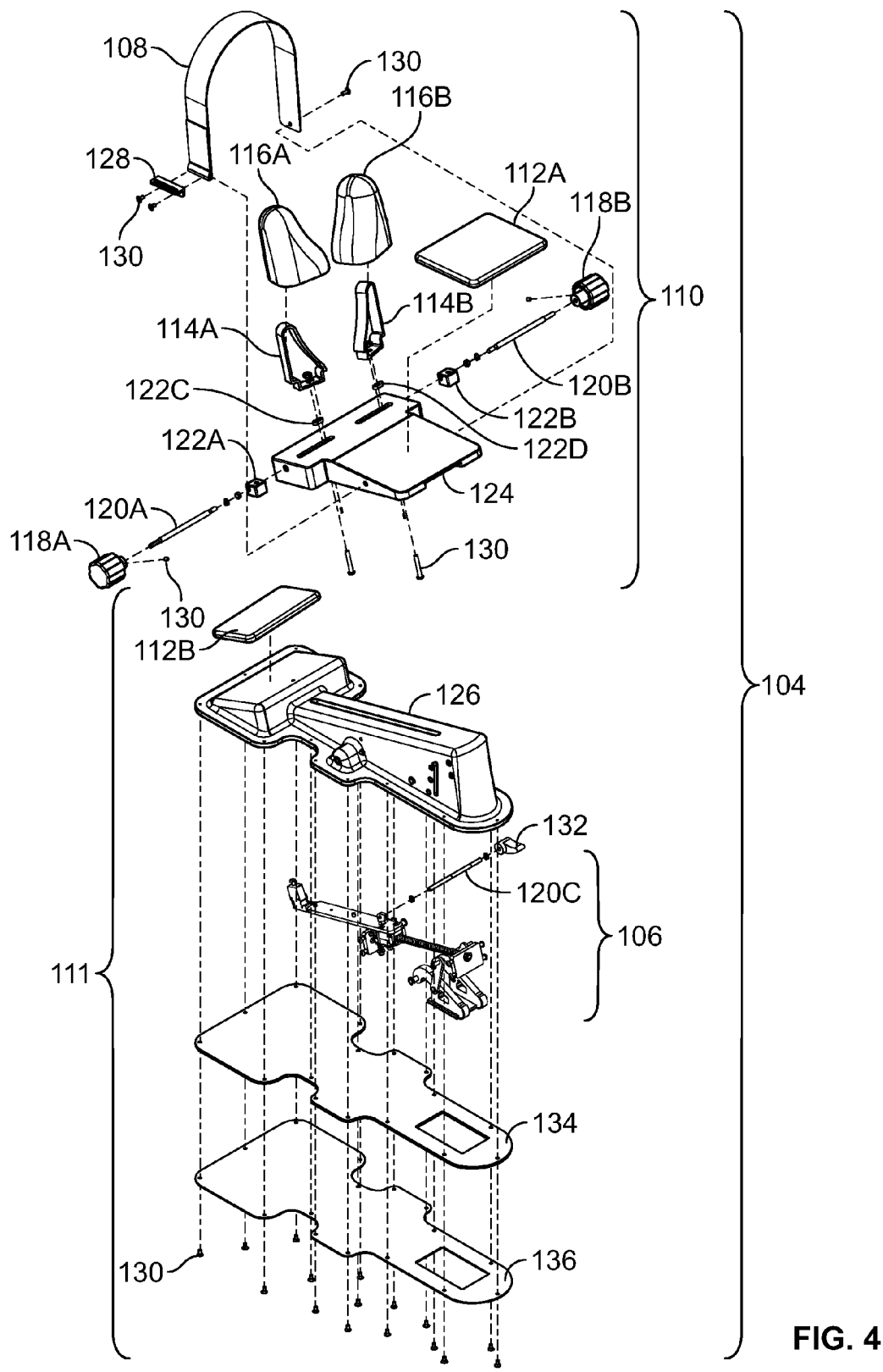
FIG. 4 illustrates an exploded view of an embodiment of FIG. 1.

Referring to FIGS. 1-14, traction system 100 may include handle assembly 102, cable assembly 138, and traction assembly 104. Any portion of traction system 100 may include the same or similar components as any of the alternative embodiments disclosed herein including the accompanying drawings. Traction assembly 104 may include plate assembly 110 and housing assembly 111. (FIG. 4). Housing assembly 111 may include drive assembly 106, pad 112B, rod 120C, housing 126, fasteners 130, release knob 132, cover 134, and bottom 136. (FIG. 4). Traction system 100 may be configured to provide traction of plate assembly 110 with respect to housing assembly 111, thereby resulting in a controlled distraction distance and/or force to the spine.

Figure 5:
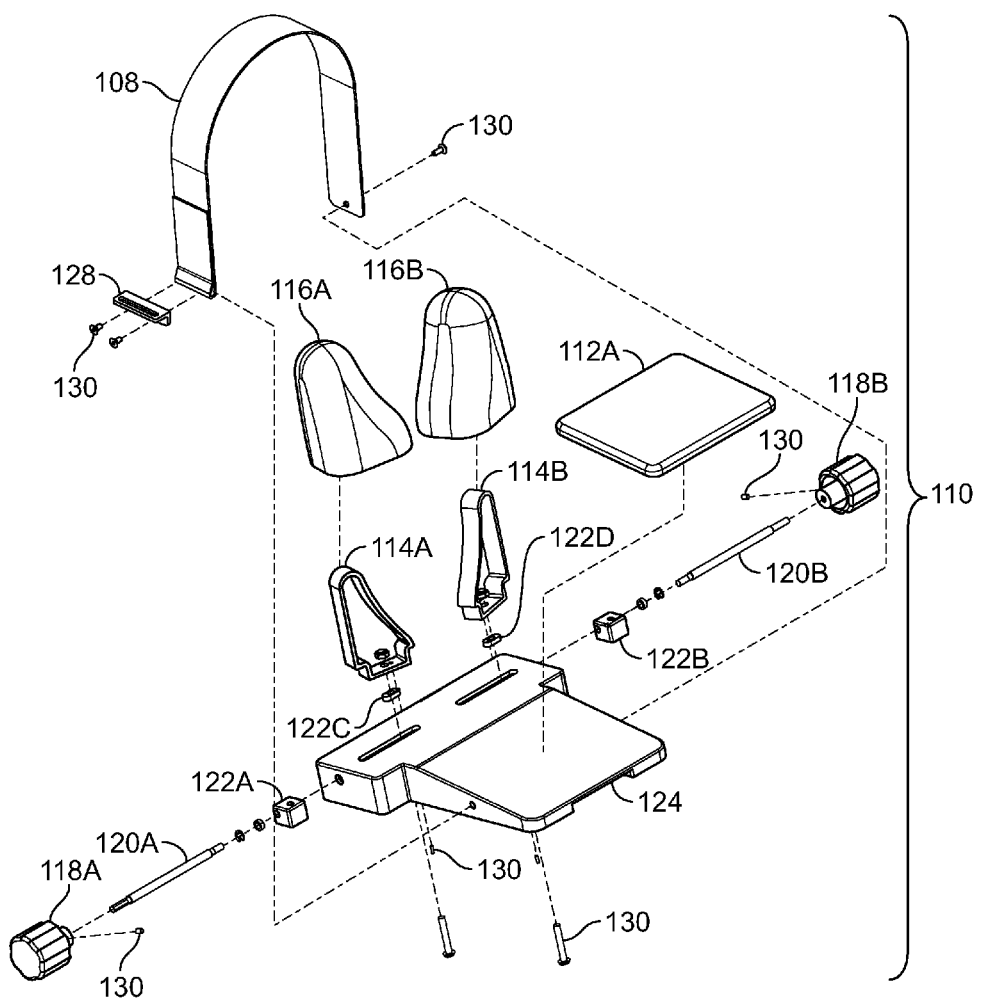
FIG. 5 illustrates an exploded view of an embodiment, for example a plate assembly.

Plate assembly 110 may include strap 108, pad 112A, inserts 114A-B, supports 116A-B, knobs 118A-B, rods 120A-B, blocks 122A-D, plate 124, bracket 128, and fasteners 130. (FIGS. 4-5). Embodiments may be shaped and/or configured to adjustably conform to a neck and/or head of a patient. Supports 116A-B and pad 112A may be configured to conform to and urge the neck and/or head with traction applied by housing assembly 111. Supports 116A-B may include anatomically shaped protrusions that may be transversely and/or angularly adjusted. A distance between supports 116A-B can be adjustable, for example, using knob 118A or 118B of plate assembly 110. Adjustability may be along or rotationally about an axis substantially parallel to the axis of rods 120. Block 122 and/or knob 118 may be internally threaded. All or a portion of rod 120 may be externally threaded. The internal threads of block 122 and/or knob 118 may engage the external threads of rod 120. Rod 120 may be positioned in plate 124 and threaded through block 120. Knob 118 may be threaded to an end of rod 120. Rotation of knob 118 may rotate rod 120 thereby engaging the internal threads of block 122 to advance block 122. Insert 114 may be screwed and/or connected to block 122 and disposed in support 116. As such, rotation of knob 118A and/or 118B may adjust supports 116A-B to engage at least a portion of the neck and/or head.

Figure 6:
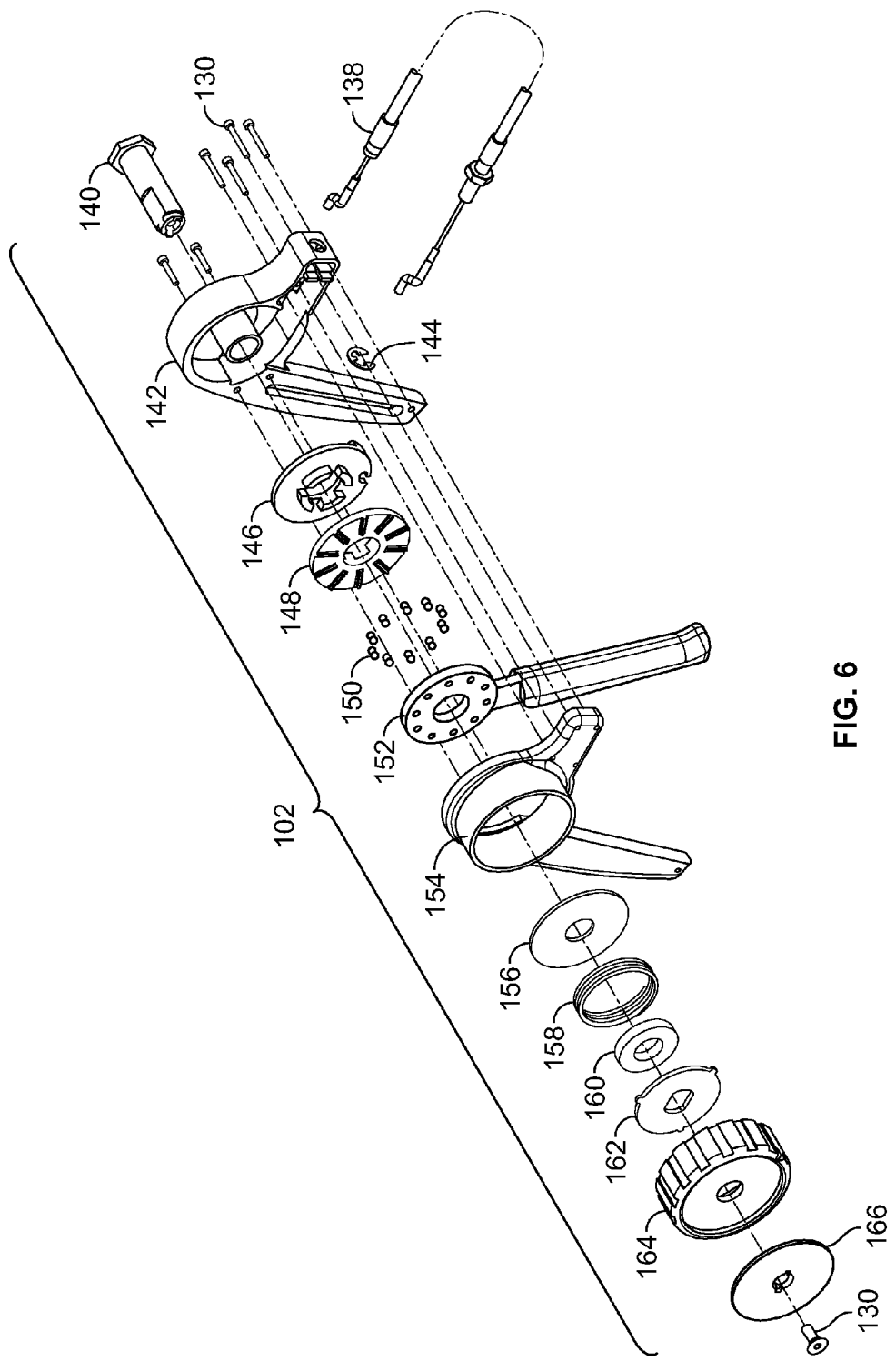
FIG. 6 illustrates an exploded view of an embodiment, for example a handle assembly.
Figure 7:
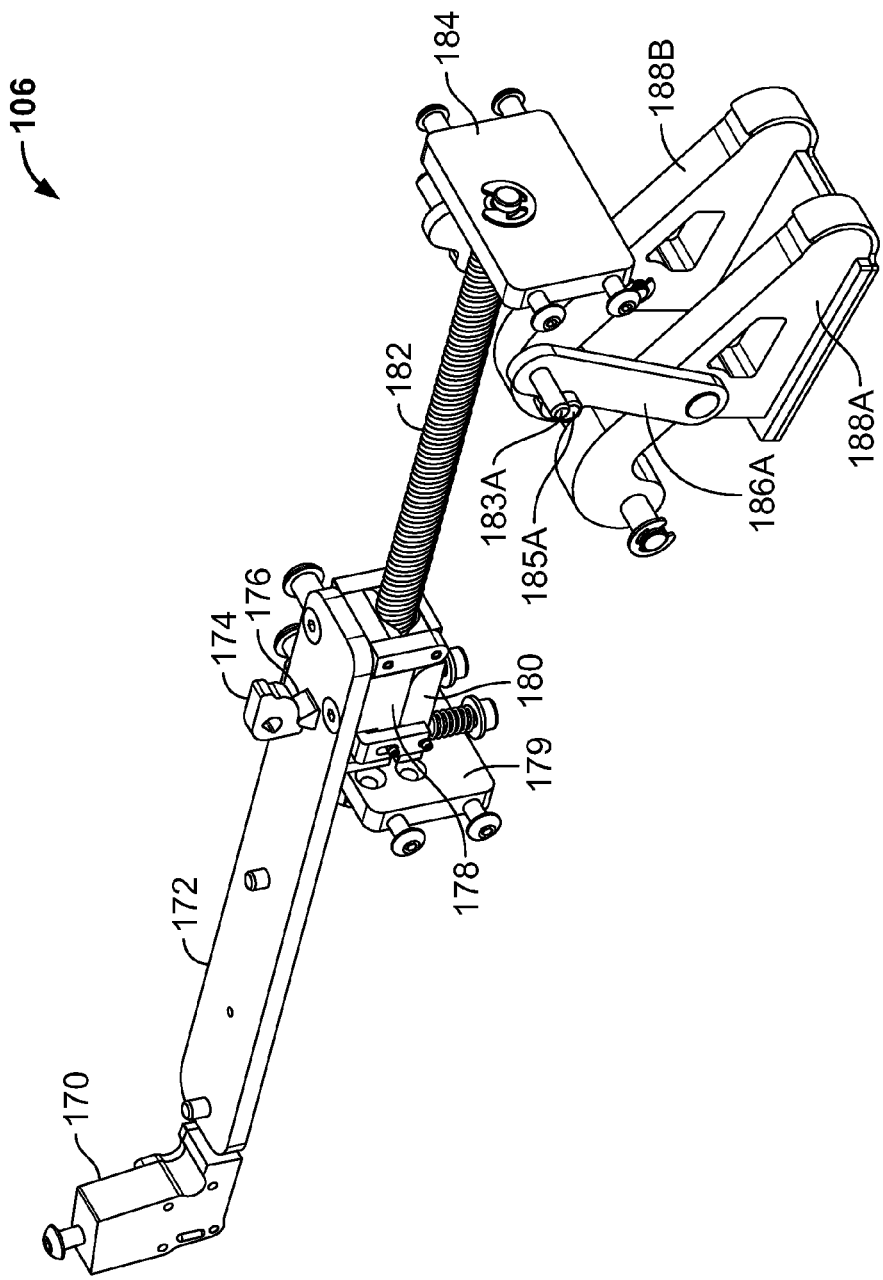
FIG. 7 illustrates an isometric view of an embodiment, for example a drive assembly.
Figure 8:
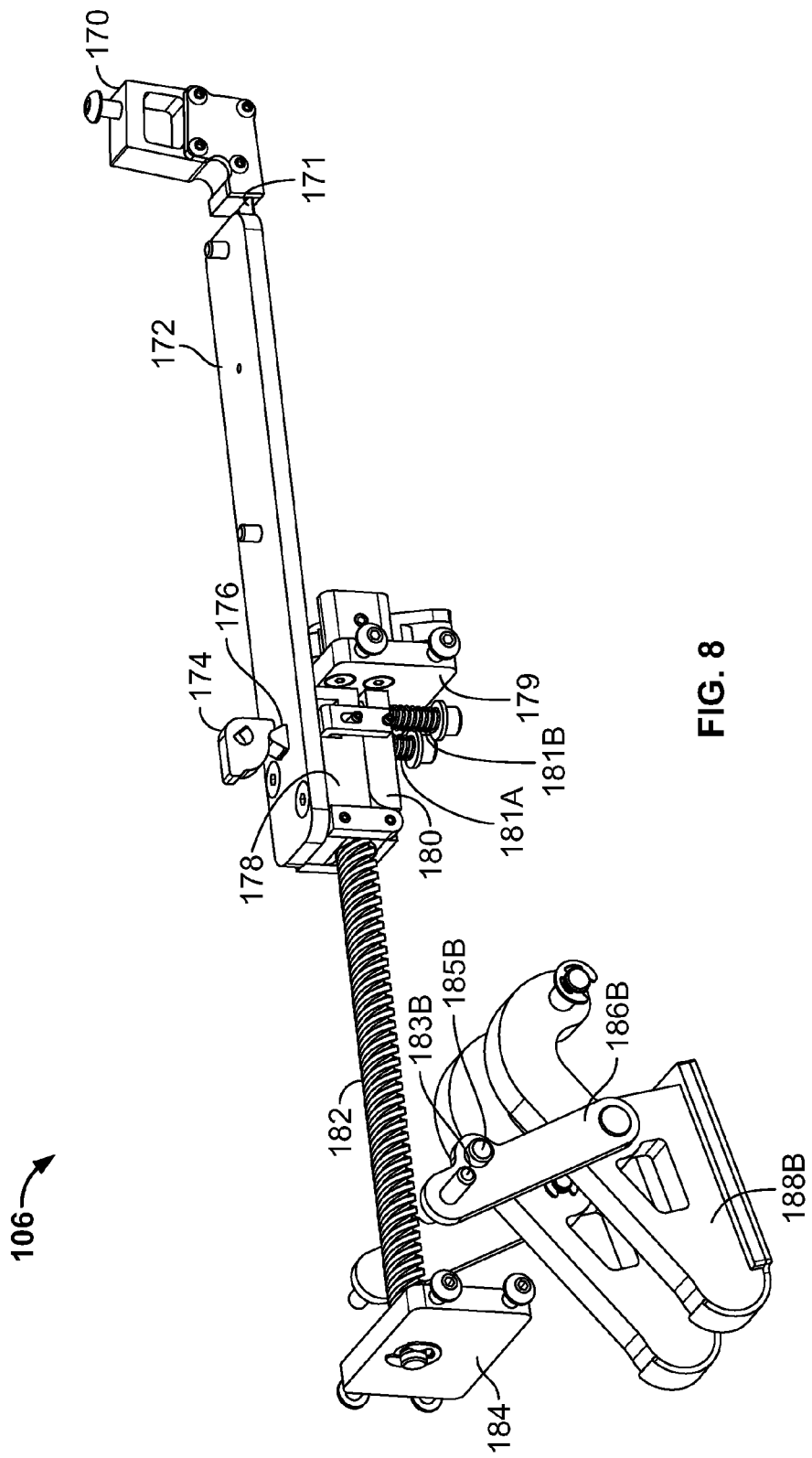
FIG. 8 illustrates an alternative isometric view of an embodiment of FIG. 7.
Figure 9:
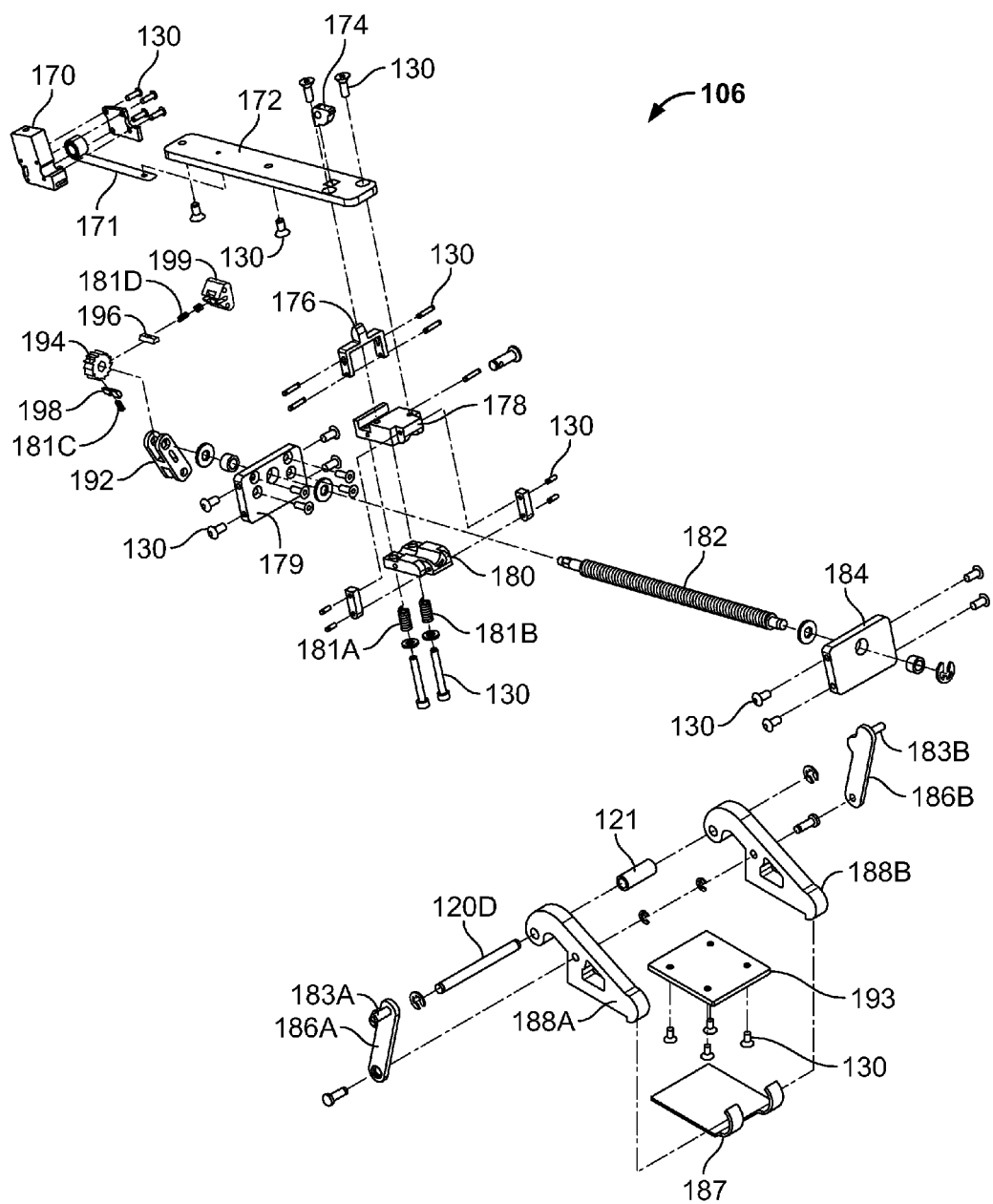
FIG. 9 illustrates an exploded view of an embodiment of FIG. 7.

Handle assembly 102 may include fasteners 130, insert 140, housing 142, clip 144, spacer 146, spacer 148, balls 150, trigger 152, housing 154, spacer 156, spring 158, spacer 160, spacer 162, knob 164, and/or spacer 166. (FIG. 6). Additional embodiments may be configured to reduce or limit traction at a set traction limit, for example with knob 164. Housing 154 may include indicia or markings corresponding to a relative position of knob 164, which indicate a desired traction limit. The traction limit may be based on when the amount of force to move drive assembly 106 with cable assembly 138 meets or exceeds the amount of force to compress spring 158 of handle assembly 102. Alternatively, the traction limit may be based on the change in length or rotation of the cable or shaft or the change in distance between plate assembly 110 and housing assembly 111. Knob 164 may be internally threaded and configured to rotate onto the external threads of housing 154 to compress spring 158, for example one or more compression spring, wave spring, or conical spring washer. Rotation of knob 164 applies compression on spring 158 thereby increasing the force that spring 158 applies to trigger 152, balls 150, and spacer 148. Balls 150 may be positioned between trigger 152 and spacer 148. Spacer 148 may include a plurality of ramps interposed by radially positioned slots around a longitudinal axis of spacer 148. (FIG. 6). Balls 150 may be positioned between the holes of trigger 152 and the slots of spacer 148. Upon actuation of trigger 152, balls 150 may be urged toward and/or up the ramps of spacer 148. If the force on spacer 148 from cable assembly 138 does not exceed the force required for balls 150 to overcome the slots of spacer 148, spacer 146 advances the drive cable of cable assembly 138 while balls 150 remain substantially in their respective slots of spacer 148. If the force on spacer 146 applied by trigger 152 meets or exceeds the force required for balls 150 to overcome the slots of spacer 148, balls 150 move up their respective ramps, further compress spring 158, and skip to the next slot of spacer 148. This causes spacer 148 to rotate with respect to trigger 152 without advancing the cable of cable assembly 138. Advancement of cable assembly 138 and/or drive assembly 106 may cease when the desired traction limit is met, thereby limiting the movement of plate assembly 110 relative to housing assembly 104. The traction applied by plate assembly 110 may be limited to the desired traction limit set by knob 164. Thus, the distraction distance and/or force may be controlled, adjusted, or limited. Handle assembly 102 may include or be used in conjunction with any embodiment disclosed herein.

Figure 10:
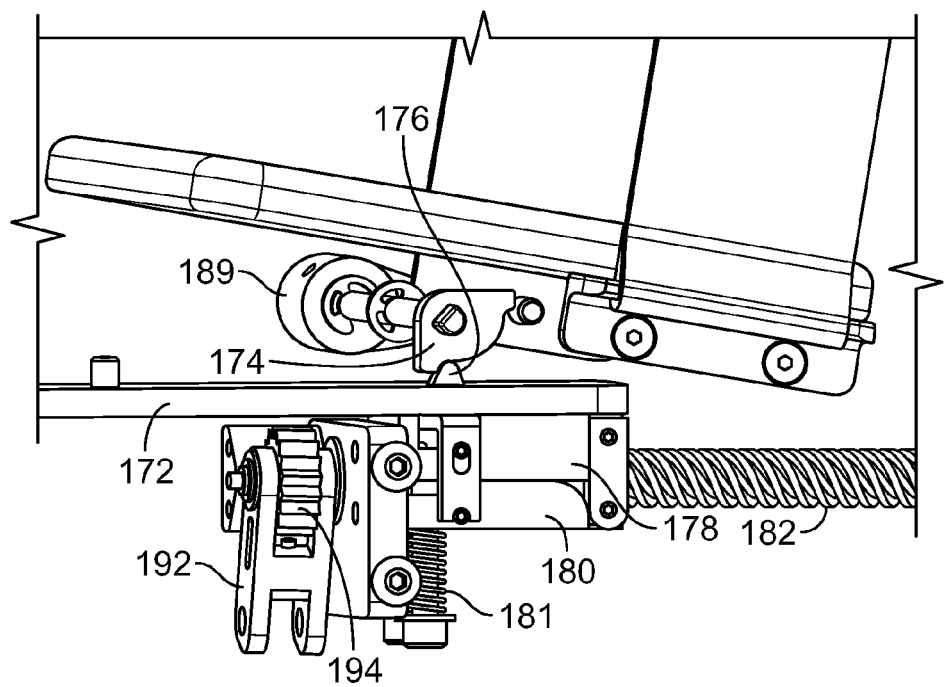
FIG. 10 illustrates a closer view of an embodiment of FIG. 7, for example the drive assembly in an engaged configuration with respect to a lead screw.
Figure 11:
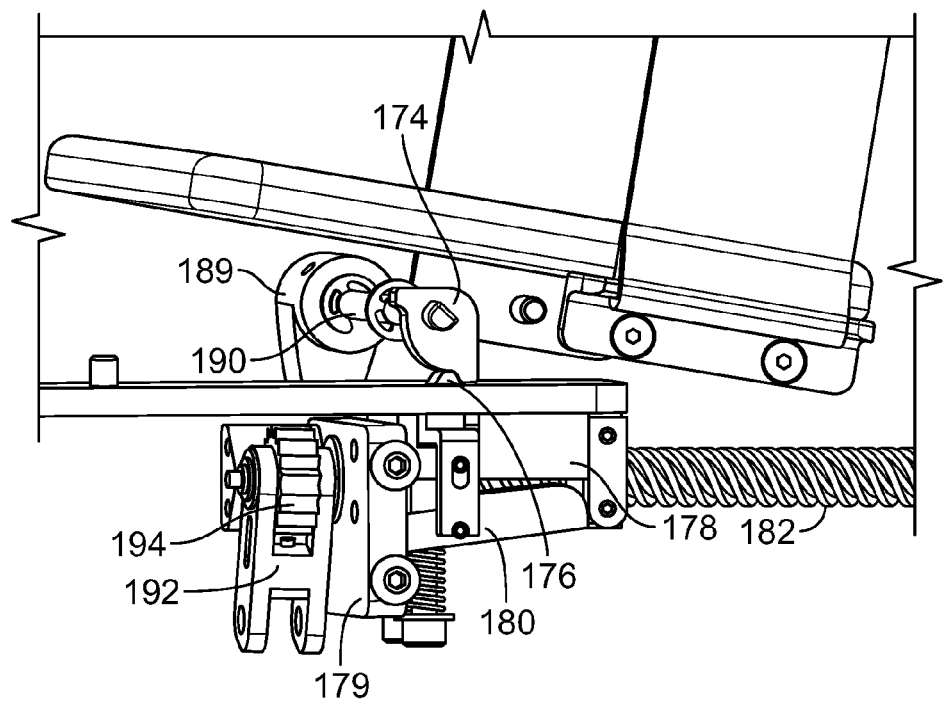
FIG. 11 illustrates a closer view of an embodiment of FIG. 7, for example the drive assembly in a released configuration with respect to the lead screw.
Figure 12:
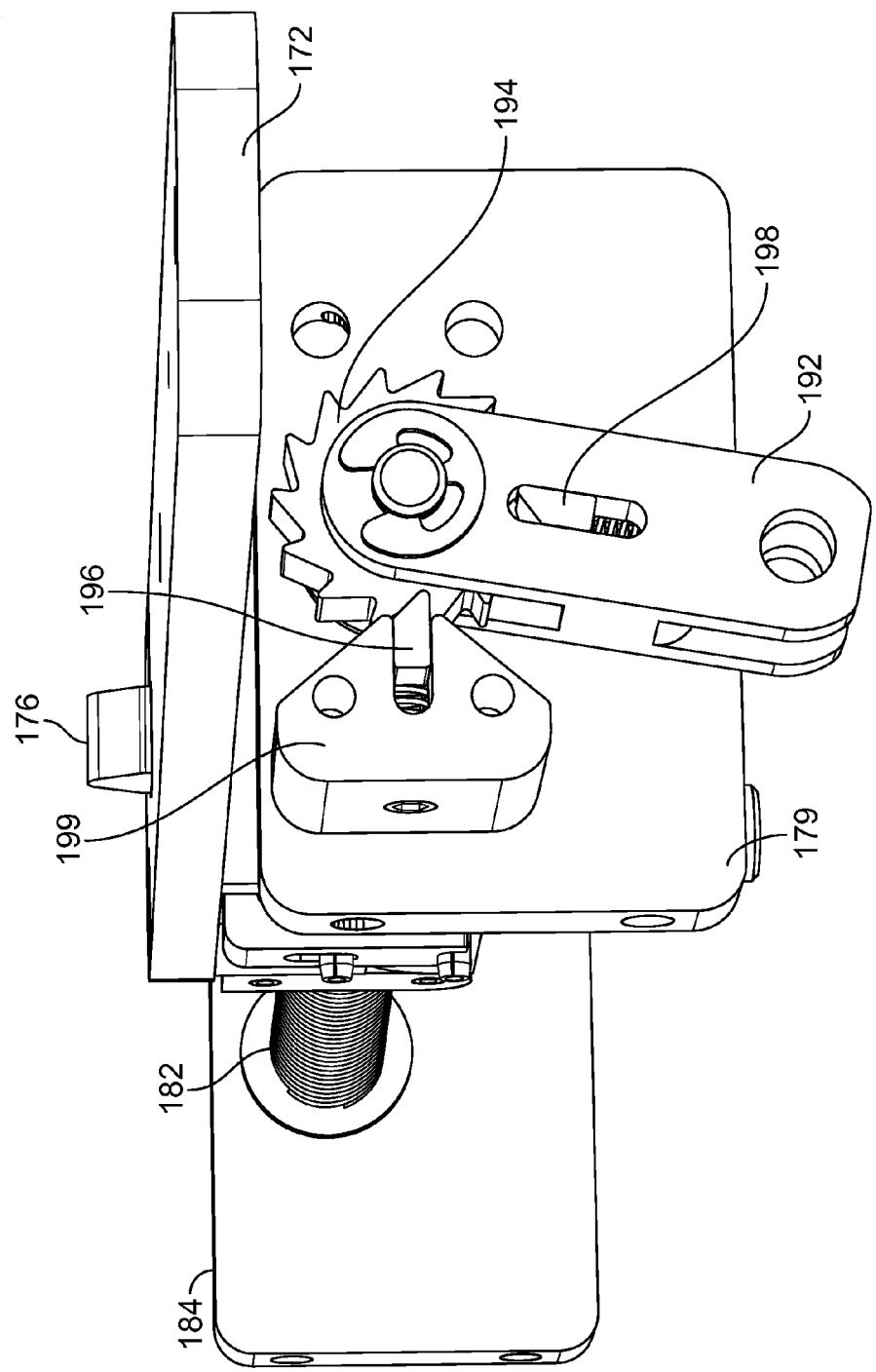
FIG. 12 illustrates a closer view of an embodiment of FIG. 7, for example, including a drive lever, drive pawn, stop pawn, and drive gear connected to the lead screw.
Figure 13:
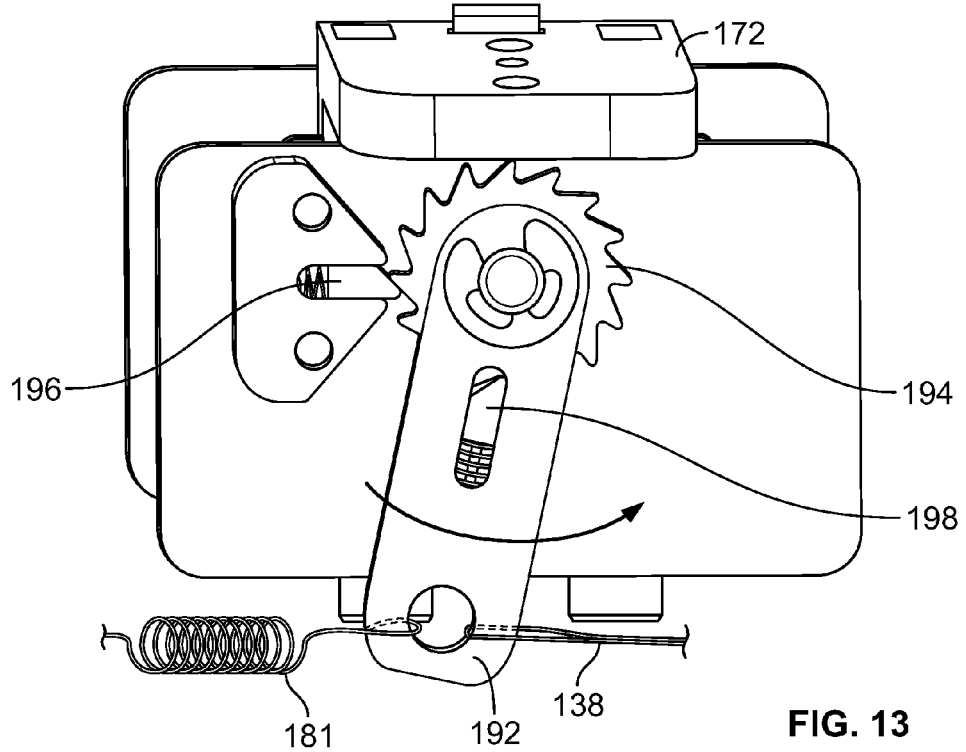
FIG. 13 illustrates a closer view of an embodiment of FIG. 7, for example in a drive configuration with the cable assembly articulating the drive lever to urge the drive pawn to rotate the drive gear.
Figure 14:
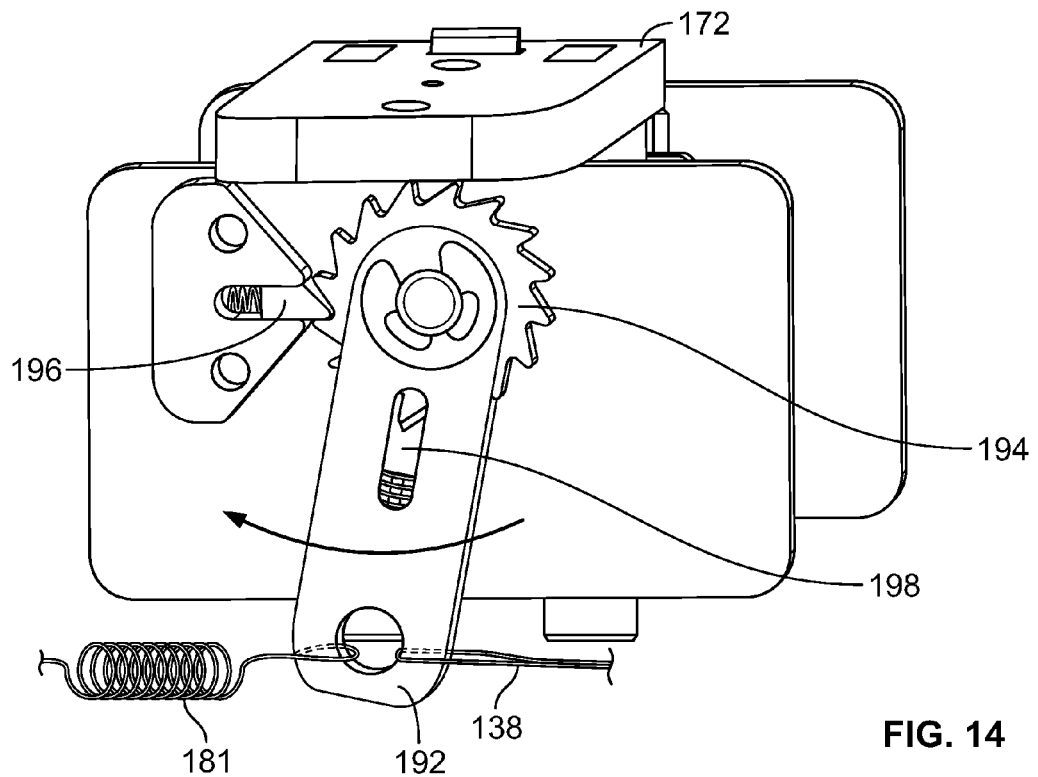
FIG. 14 illustrates a closer view of an embodiment of FIG. 7, for example in a reset configuration with the stop pawn holding the drive gear while the spring resets the drive lever and drive pawn.

Drive assembly 106 may include retractor 170, retractor spring 171, drive plate 172, release cam 174, release bracket 176, upper member 178, plate 179, lower member 180, release springs 181, lead screw 182, angle button 183, plate 184, angle pin 185, angle arm 186, base arm 188, release lever 189, rod 190, lever 192, gear 194, stop pawn 196, drive pawn 198, and arm 199. (FIG. 7-14). Drive plate 172 may be connected to plate assembly 110 and cable assembly 138. Cable assembly 138 may be connected to and/or configured to actuate lever 192. (FIGS. 12-14). A first portion of lever 192 may be connected to gear 194, which may be configured to rotate lead screw 182. A second portion of lever 192 may be connected to spring 181 and cable assembly 138, which may be configured to apply opposing forces to articulate lever 192. Gear 194 may include teeth and/or may be operatively connected to drive pawn 198 and stop pawn 196, both of which may be spring loaded. Drive pawn 198 may be configured to rotate gear 194 in a first direction with actuation from cable assembly 138. Stop pawn 196 may be configured to stop rotation of gear 194 in an opposite, second direction while lever 192 articulates to the initial position with the force from spring 181. Trigger 152 may be repeatedly actuated (i.e. squeezed) to increase traction until a clutch of handle assembly 106 slips at the set traction limit.

Further embodiments may be configured to increase traction, for example to increase a distraction distance between portions of a cervical spine. Trigger 152 of the handle assembly 102 may be actuated to advance plate assembly 110 relative to the housing assembly 111. With drive pawn 198 engaged into gear 194 connected to lead screw 182, actuation of trigger 152 urges cable assembly 138 to articulate lever 192 (FIG. 13) thereby rotating lead screw 182 against the internal threads of upper member 178 and/or lower member 180 to advance drive plate 172 that is connected to plate assembly 110. This results in movement of plate assembly 110 along housing assembly 111 to increase traction. (FIGS. 11-12). After trigger 152 is released, spring 181 recoils lever 192 to an initial position. (FIG. 13). As lever 192 moves relative to gear 194 to recoil to the initial position under a spring force, stop pawn 196 ratchets over a tooth of gear 194 and drops behind the next tooth of gear 194 thereby resisting rotation of gear 194 in the opposite direction. As a result, the plate assembly 110 is moved relative to the housing assembly 111 to apply a traction force to the neck including the cervical spine. After traction is applied, the position of plate assembly 110 may be retained relative to housing assembly 111 to maintain traction. If increased traction is desired, additional activations of trigger 152 may further advance plate assembly 110 to increase traction.

Drive assembly 106 may be configured to releasably engage plate assembly 110, for example to longitudinally adjust a position of plate assembly 110. Drive assembly 106 may be configured to releasably engage lead screw 182 with release knob 132. (FIGS. 10-12). When the drive assembly 106 is engaged, one or more springs 181 urge lower member 180 toward upper member 178. (FIG. 10). To release upper member 178 and/or lower member 180 from each other, release knob 132 may be rotated thereby pressing the release cam 174 downward on release bracket 176. (FIG. 11). Release bracket 176 presses down on the pins in lower member 180 to pivot lower member 180 away from upper member 178. This causes an internal threaded area in upper member 178 and/or lower member 180 to disengage from lead screw 182 thereby allowing upper member 178 and/or lower member 180 to slide with respect to lead screw 182. After release knob 132 is released, springs 181 urge upper member 178 and/or lower member 180 to re-engage lead screw 182.

Housing assembly 111 may have an adjustable traction angle with respect to a support surface, for example by pressing button 183 to disengage pin 185 from one or more holes in housing 126. This may adjust a traction angle of housing assembly 111 relative to the support surface. Housing assembly 111 may be configured to provide any traction angle, for example at or between any of 0, 5, 10, 15, 20, 25, 30, 35, 40, and/or 45 degrees. Base arm 188 may extend from and/or push against the support surface to adjust the angle of housing 126. Housing 126 may include a plurality of holes to receive pin 185 of angle arm 186. By pressing button 183 of angle arm 186 to disengage pin 185 from housing 126, base arm 188 may be adjusted with respect to housing 126. Housing 126 may be positioned near a hole corresponding to the desired traction angle. For example, embodiments may include a top hole providing a traction angle of about 15 degrees, a top middle hole providing a traction angle of about 20 degrees, a bottom middle hole providing a traction angle of about 25 degrees, and/or a bottom hole providing a traction angle of about 30 degrees. Upon release of button 183 of a selected hole, pin 185 may re-engage housing 126 to provide the desired traction angle.

Figure 15:
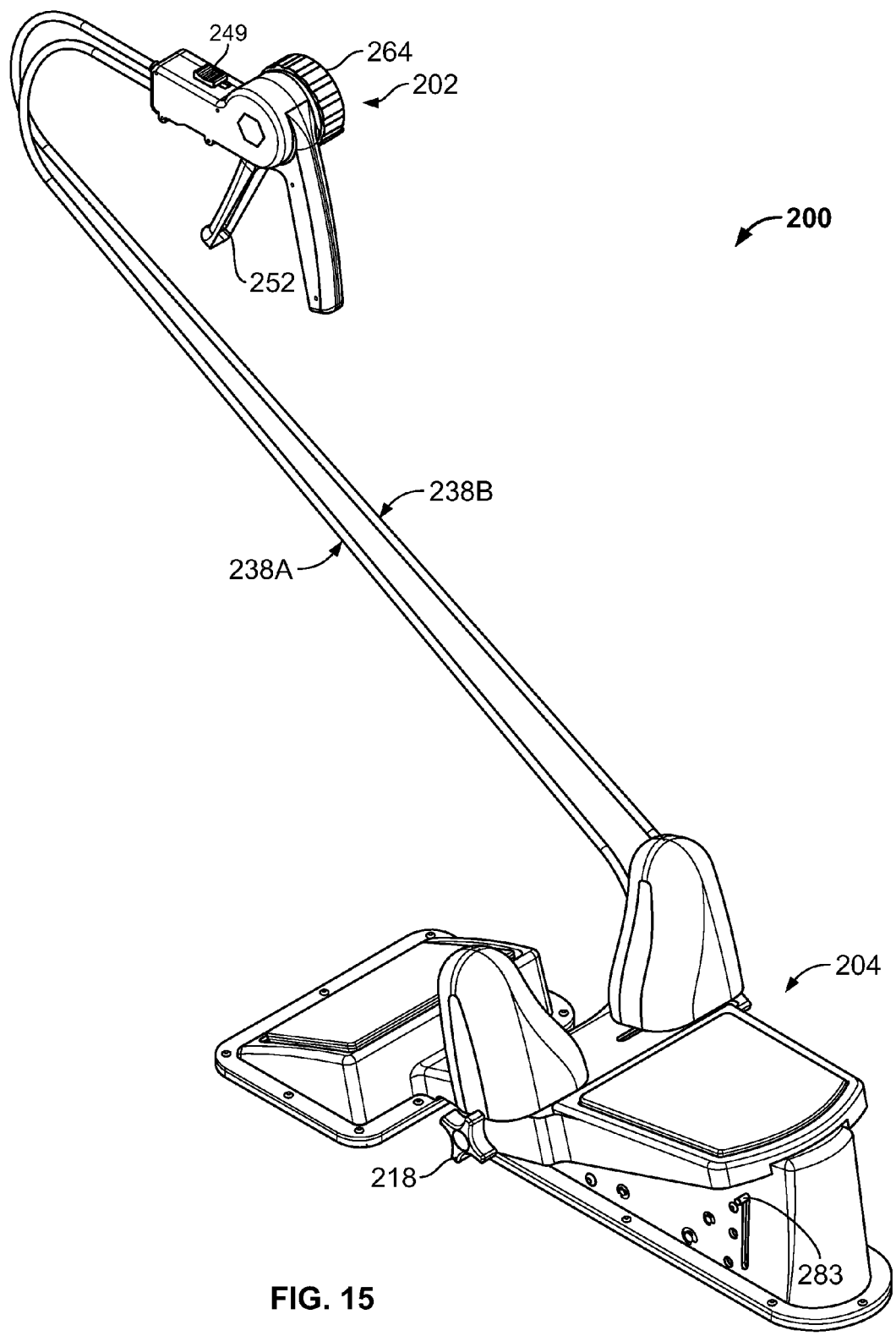
FIG. 15 illustrates an embodiment, for example, an alternative traction system.
Figure 16:
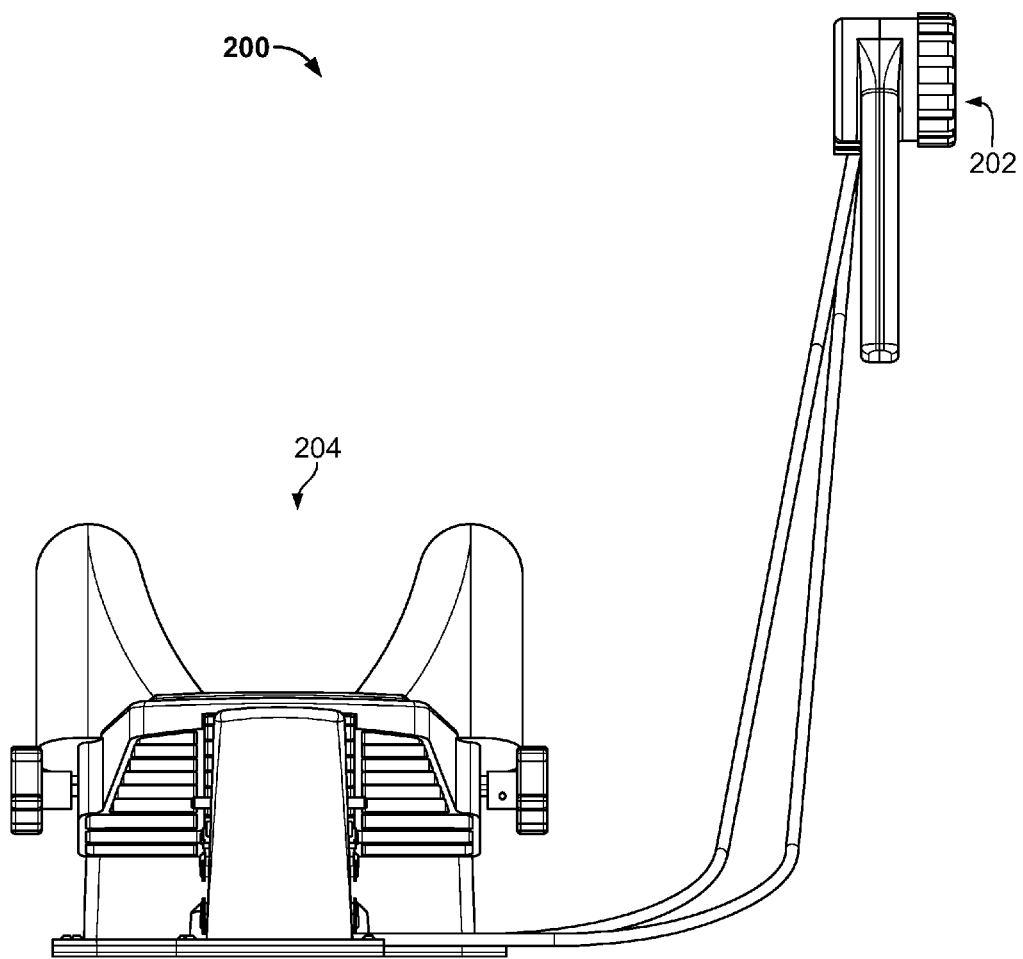
FIG. 16 illustrates a rear view of an embodiment of FIG. 15.
Figure 17:
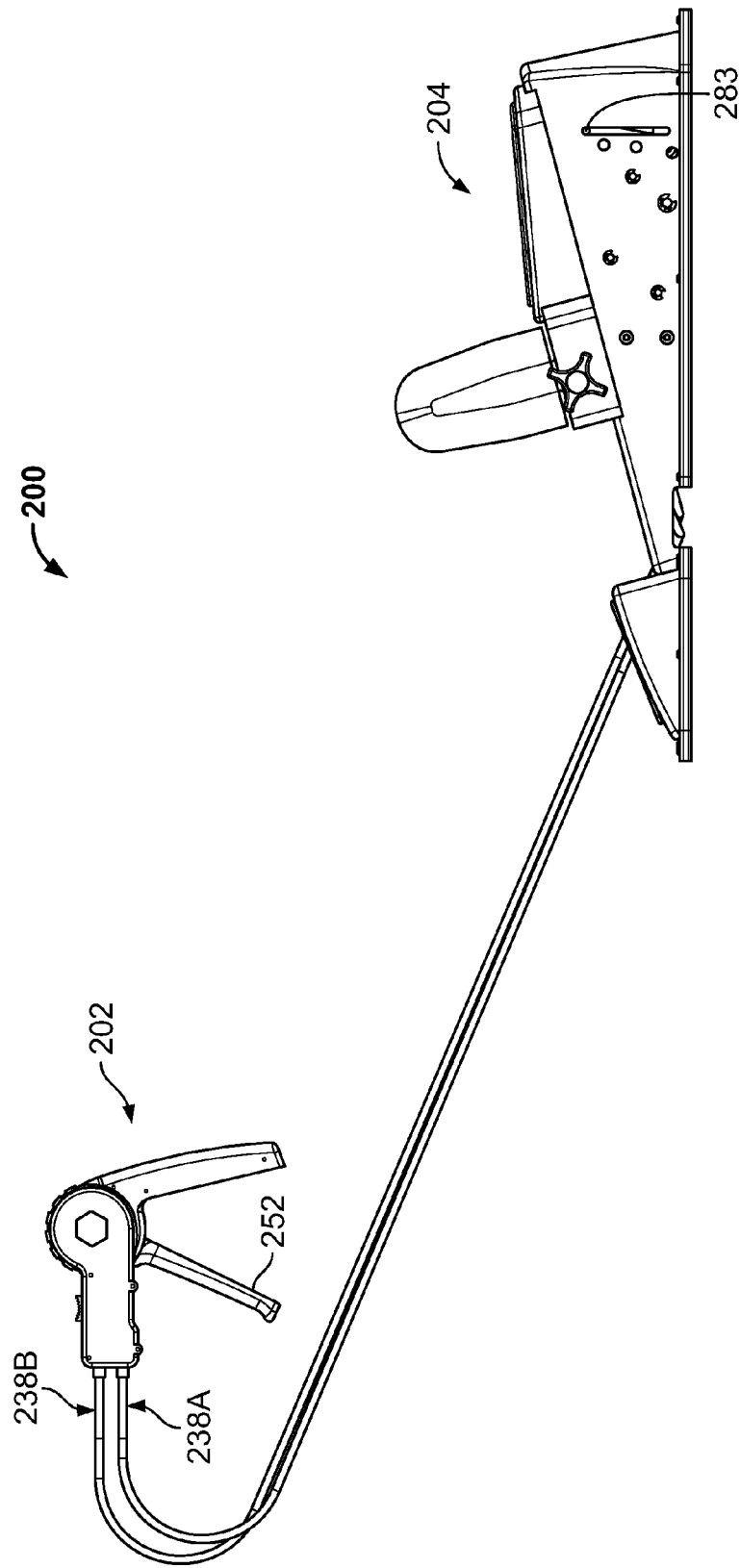
FIG. 17 illustrates a side view of an embodiment of FIG. 15.
Figure 18:
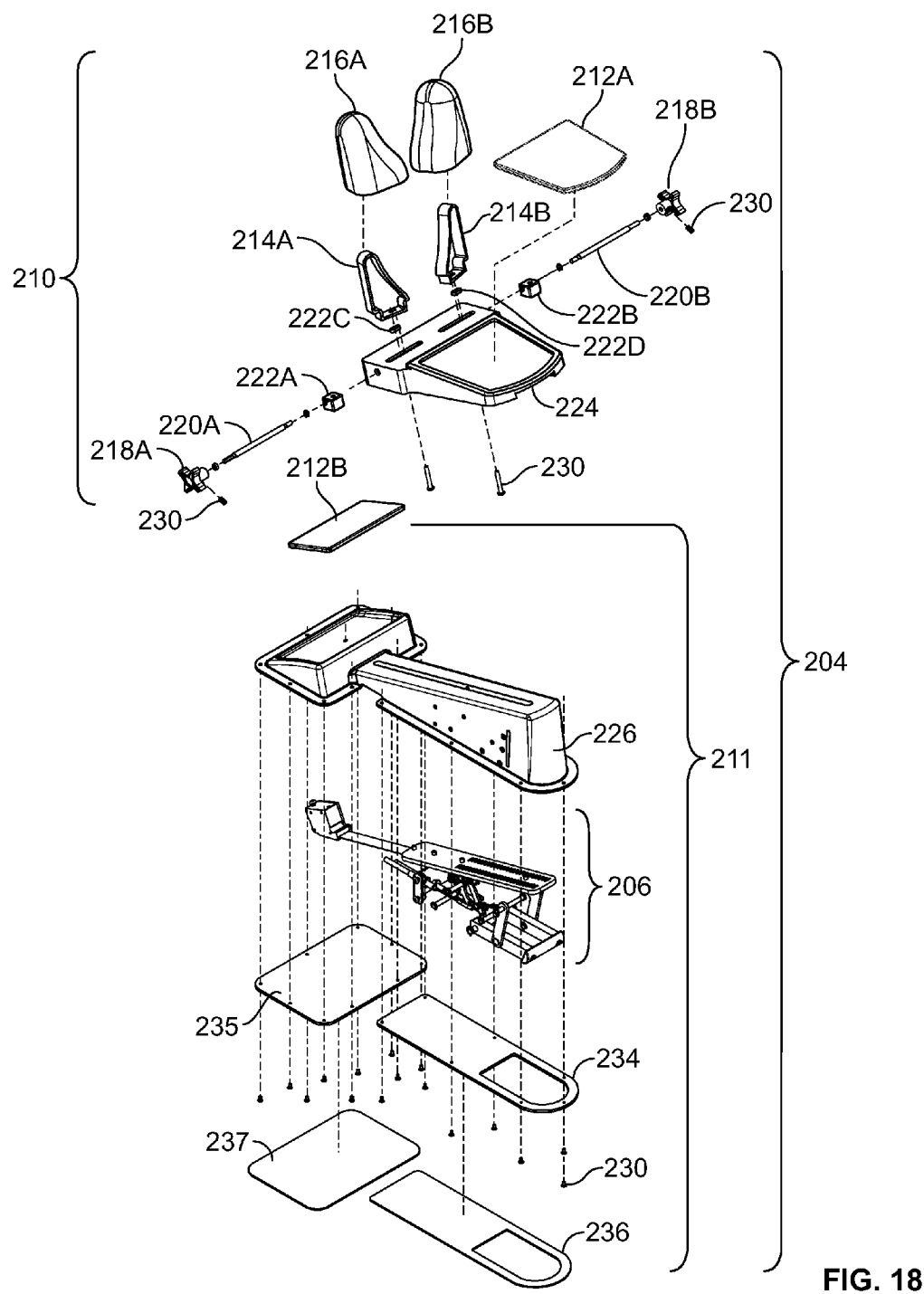
FIG. 18 illustrates an exploded view of an embodiment of FIG. 15.

With reference to FIGS. 15-24, traction system 200 may include handle assembly 202, cable assembly 238, and traction assembly 204. Any portion of traction system 200 may include the same or similar components as any of the alternative embodiments disclosed herein including the accompanying drawings. Traction assembly 204 may include plate assembly 210 and housing assembly 211. (FIGS. 15-17). Plate assembly 210 may include strap 208, pad 212A, inserts 214A-B, supports 216A-B, knobs 218A-B, rods 220A-B, blocks 222A-D, plate 224, and/or fasteners 230. (FIG. 18). Housing assembly 211 may include drive assembly 206, pad 212B, housing 226, fasteners 230, cover 234, cover 235, bottom 236, and/or bottom 237. (FIG. 18).

Figure 19:
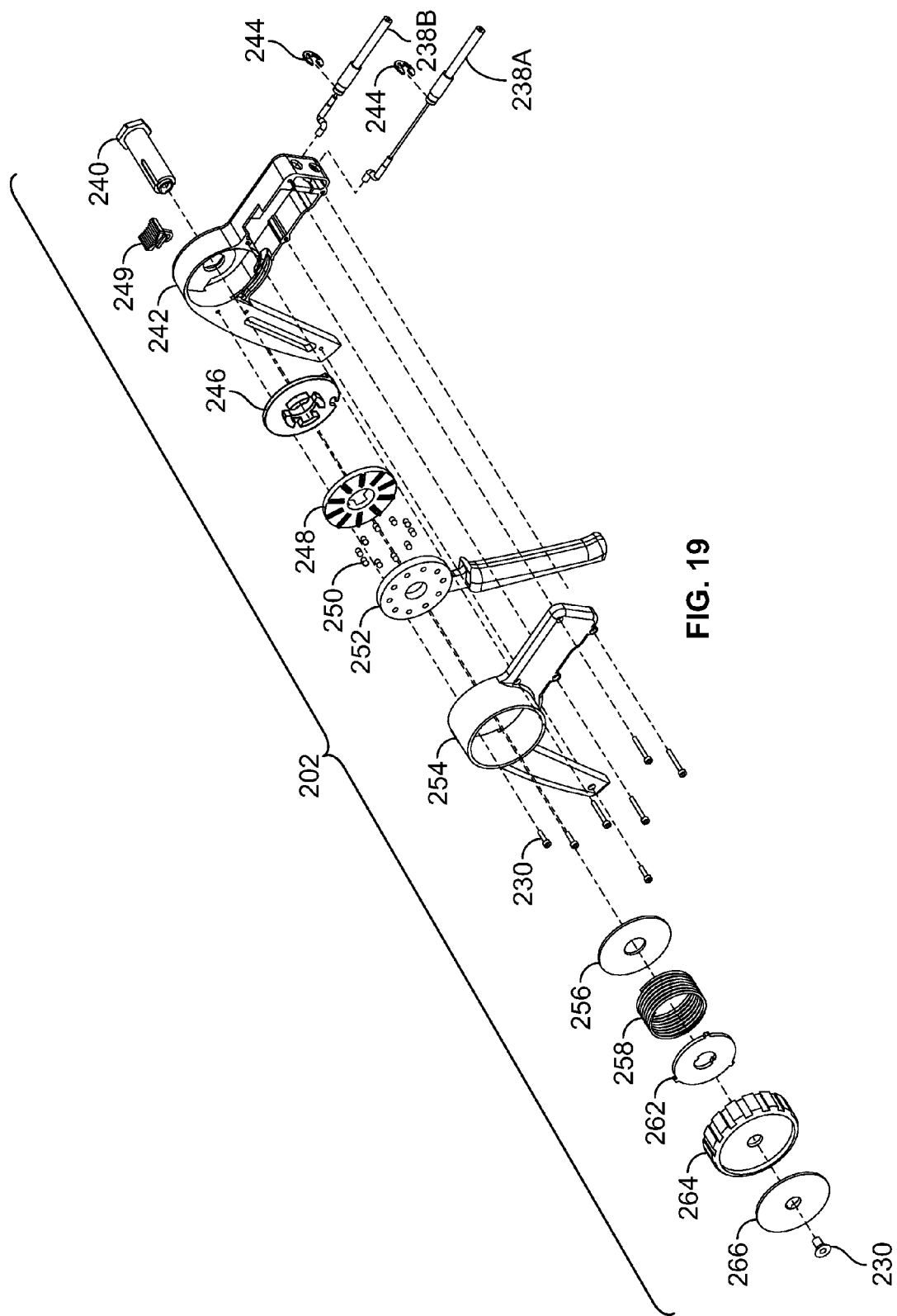
FIG. 19 illustrates an exploded view of an embodiment, for example an alternative handle assembly.
Figure 20:
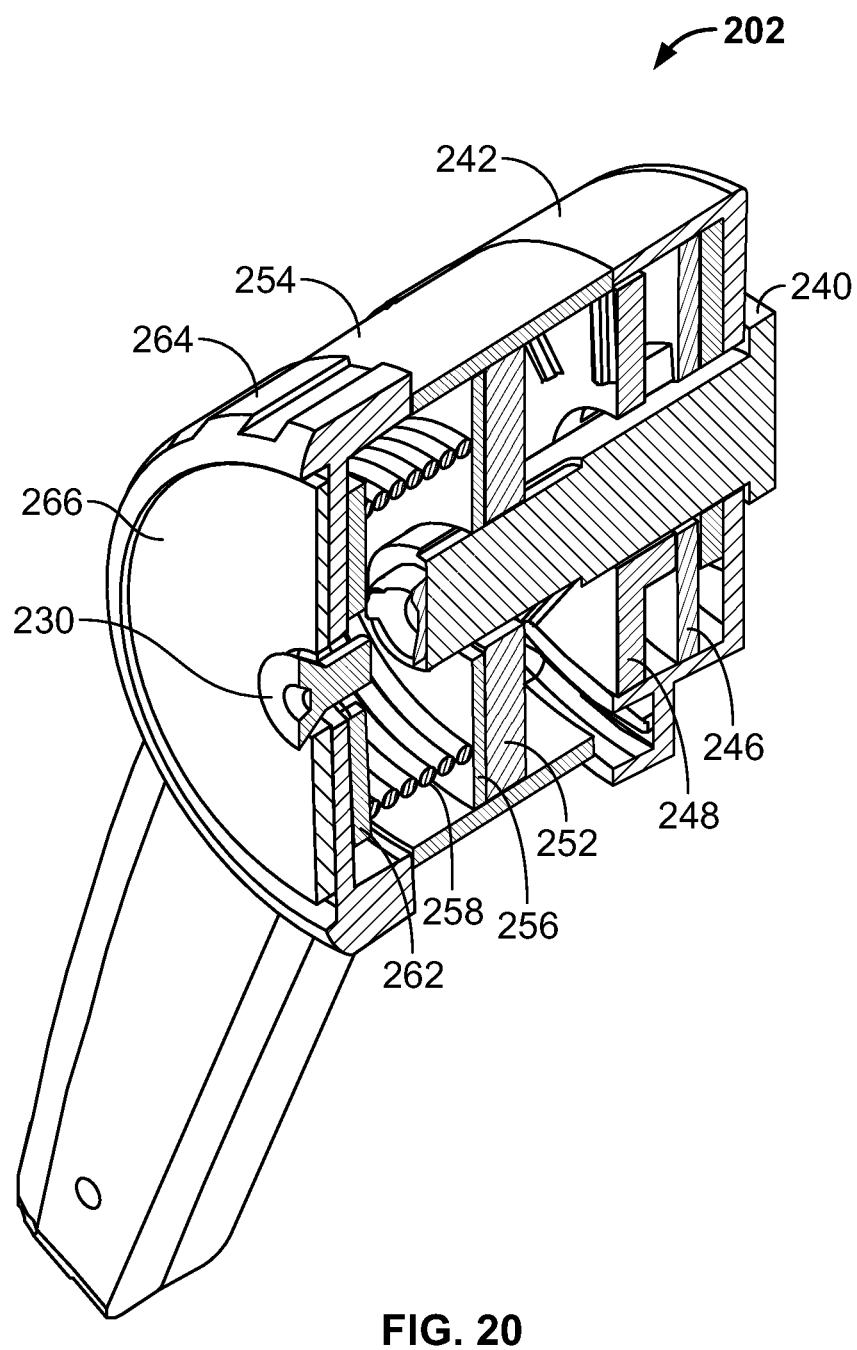
FIG. 20 illustrates a section view of an embodiment of FIG. 19.
Figure 21:
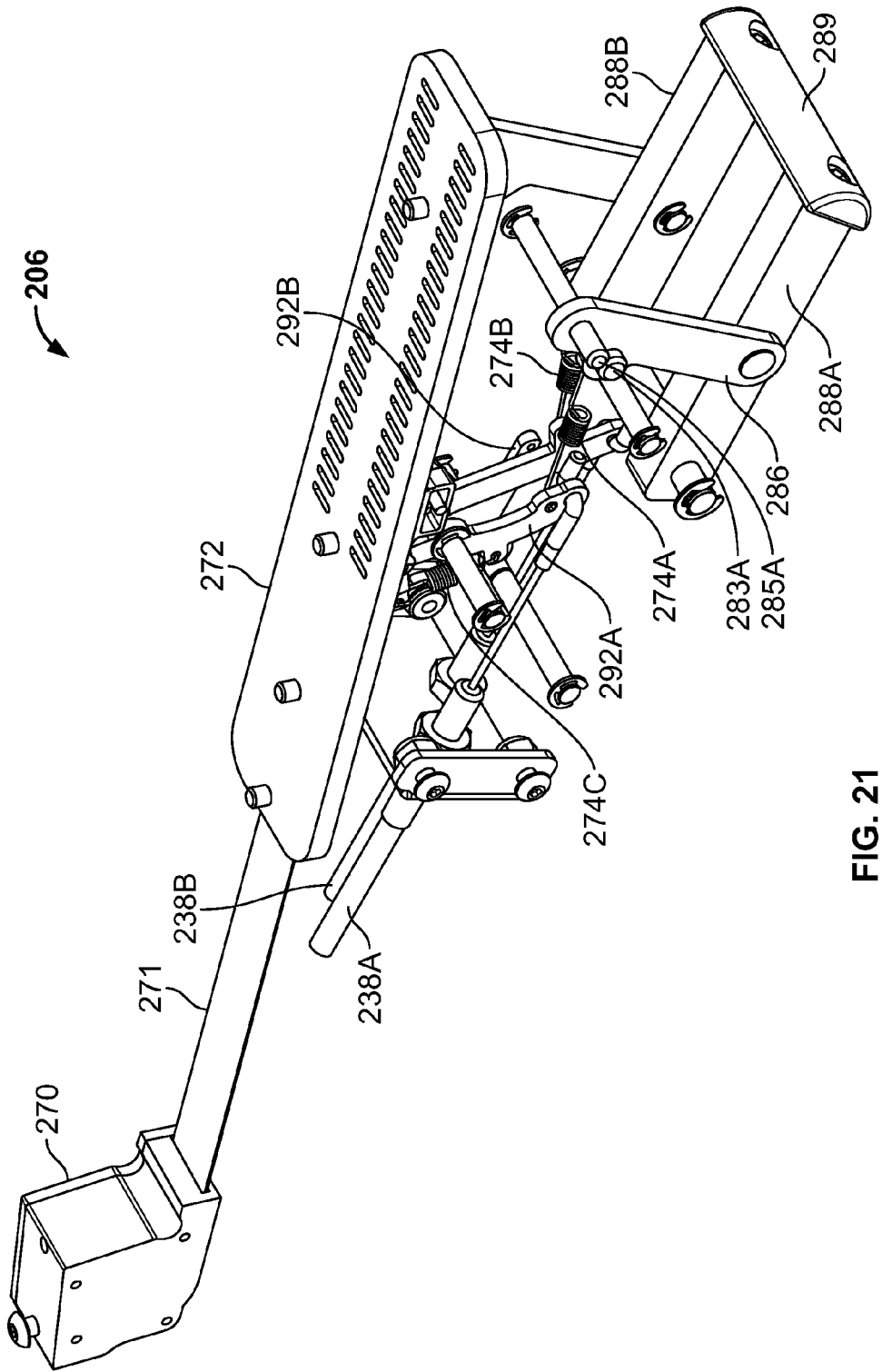
FIG. 21 illustrates an isometric view of an embodiment, for example an alternative drive assembly.
Figure 22:
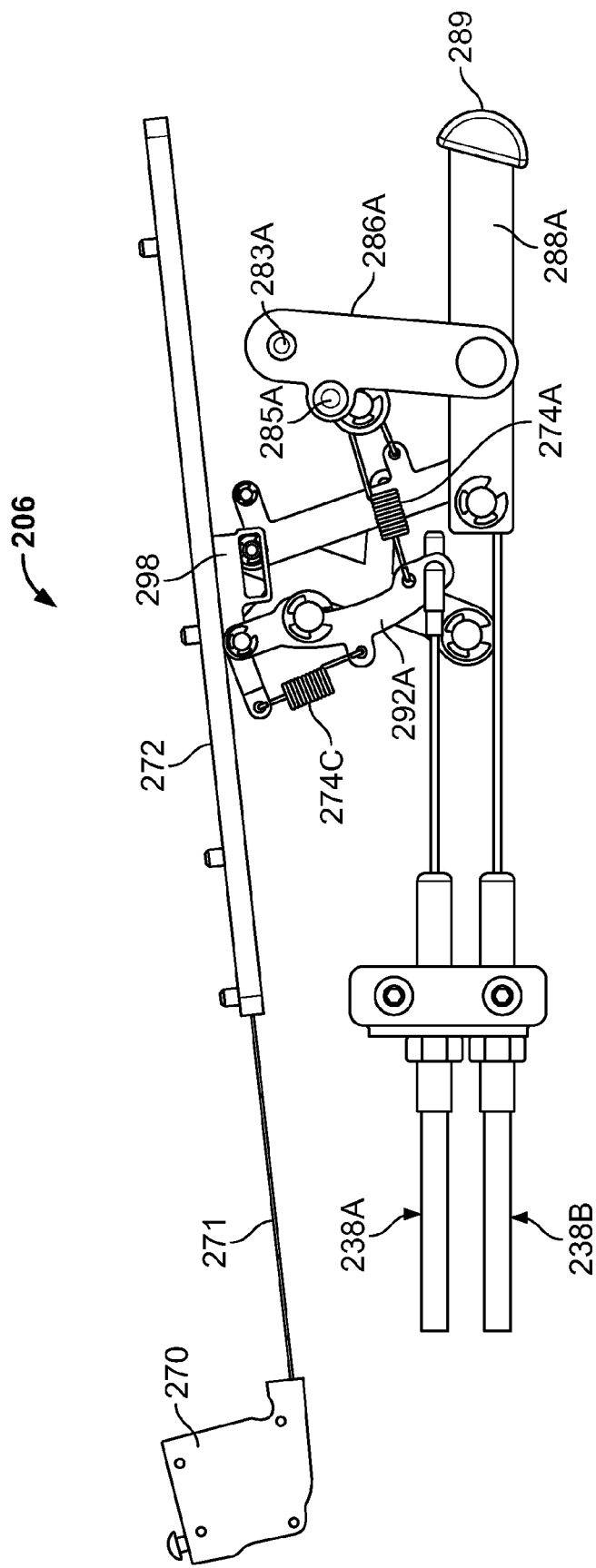
FIG. 22 illustrates a side view of an embodiment of FIG. 21.
Figure 23:
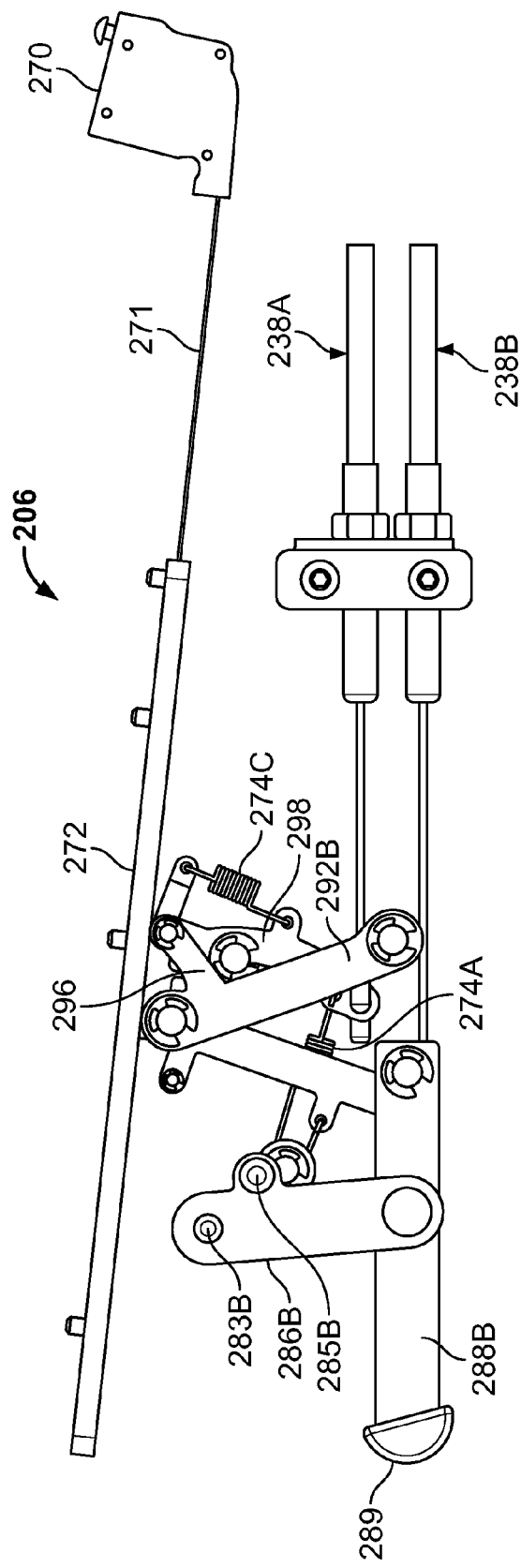
FIG. 23 illustrates an opposite side view of an embodiment of FIG. 21.
Figure 24:
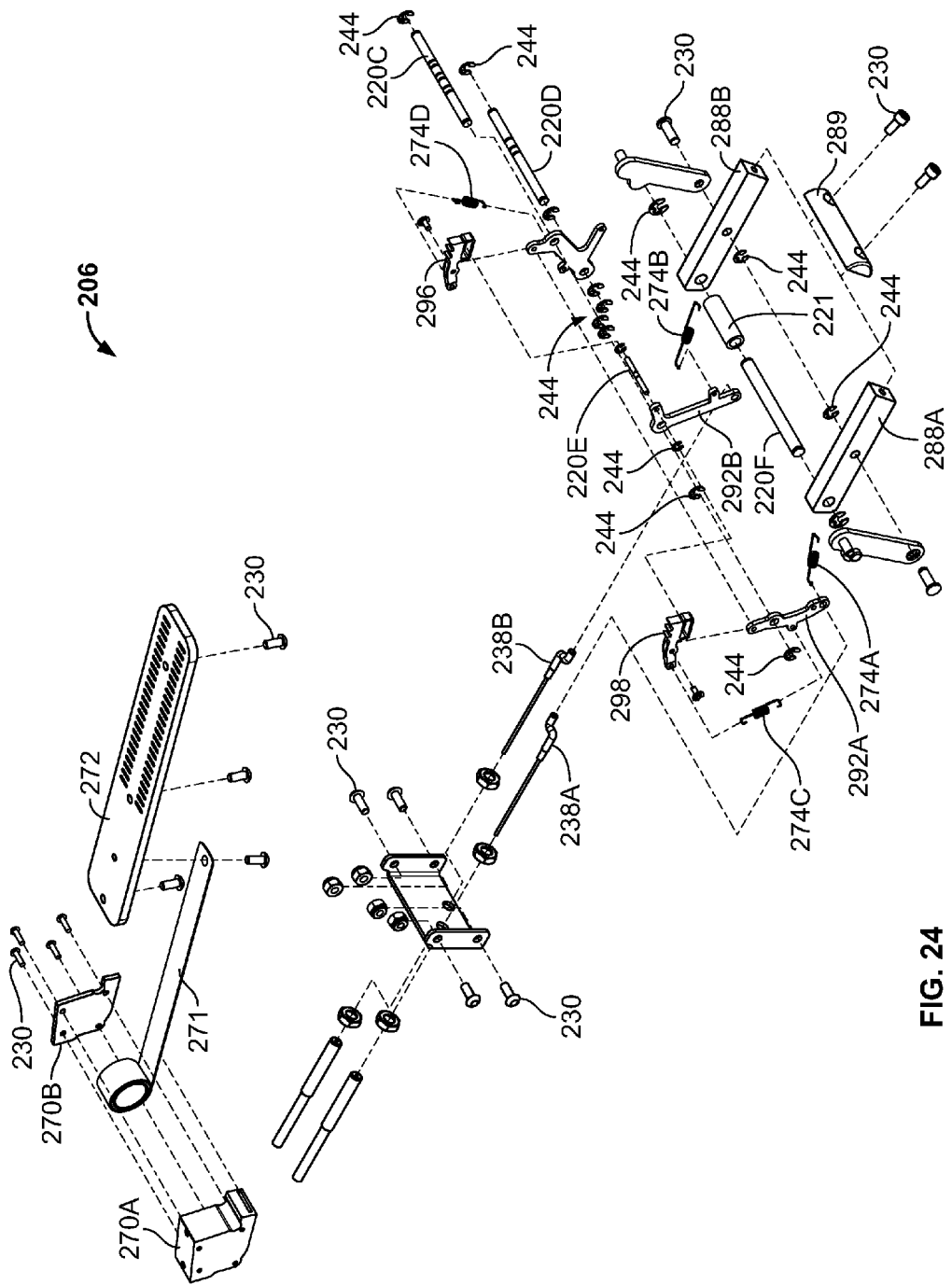
FIG. 24 illustrates an exploded view of an embodiment of FIG. 21.
Figure 25:
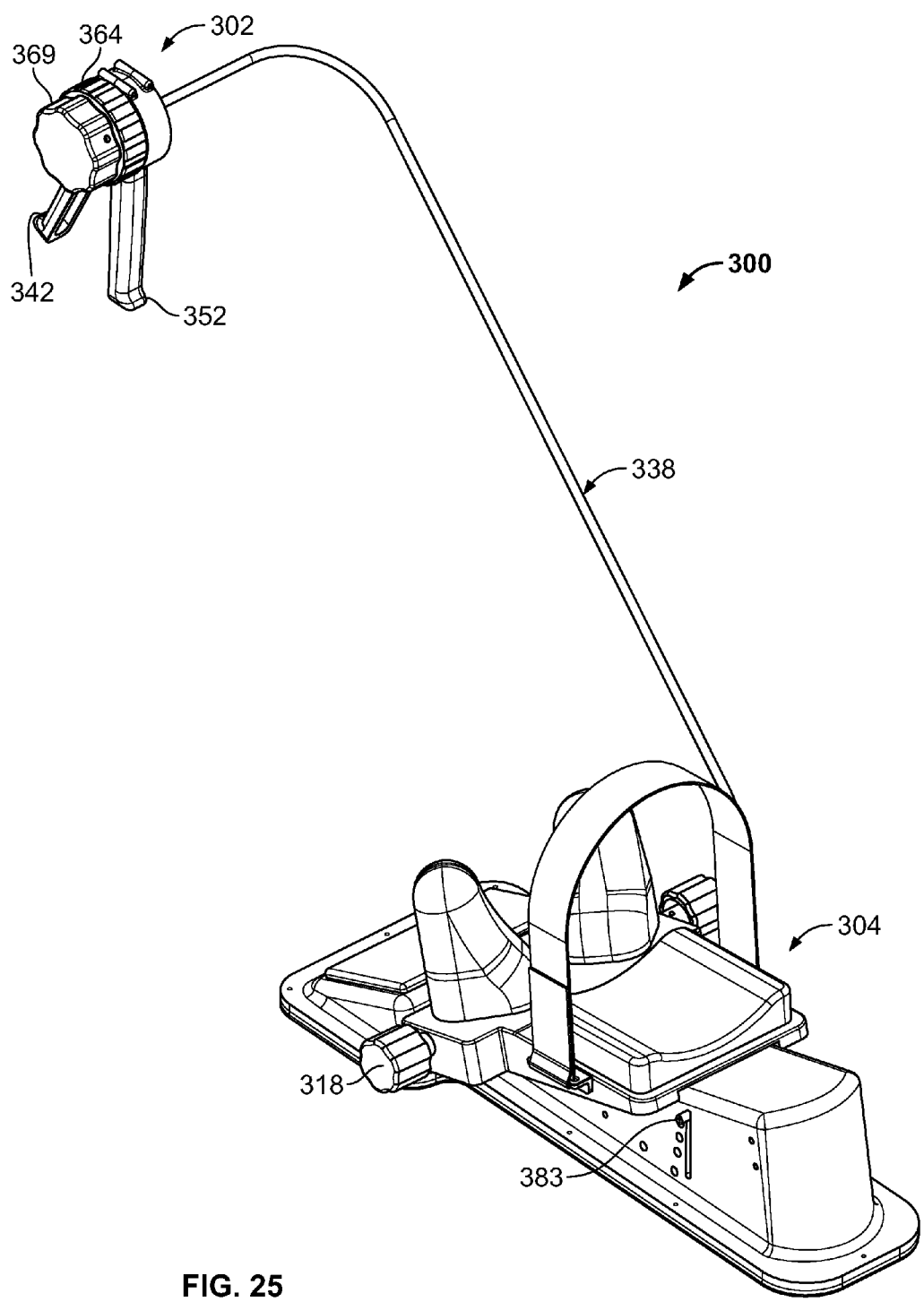
FIG. 25 illustrates an isometric view of an embodiment, for example an alternative traction system in a contracted configuration.
Figure 26:
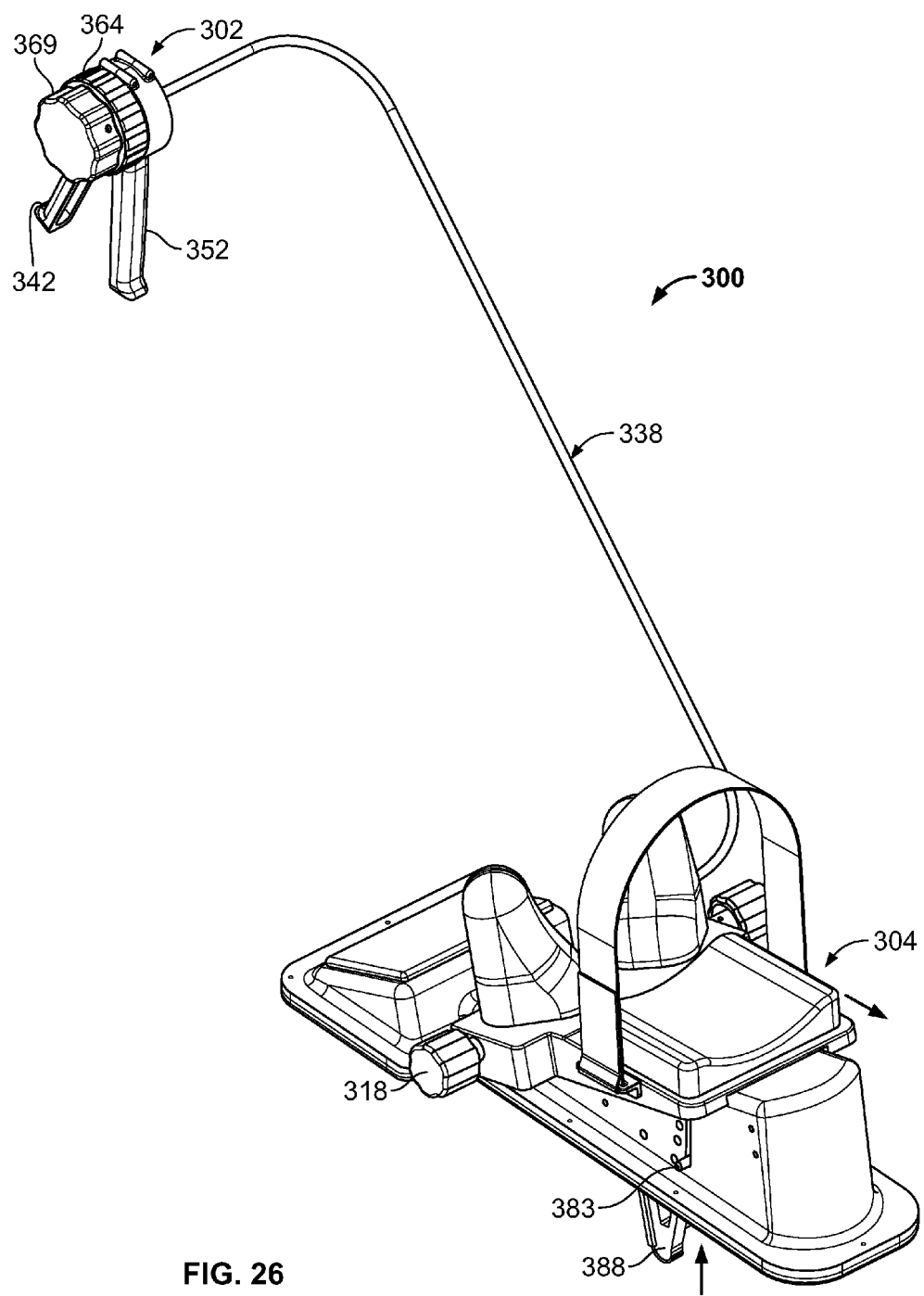
FIG. 26 illustrates an isometric view of an embodiment, for example, in an extended configuration and with an increased traction angle.

Handle assembly 202 may include fasteners 230, cable assembly 238A, cable assembly 238B, insert 240, housing 242, clip 244, spacer 246, spacer 248, release 249, balls 250, trigger 252, housing 254, spacer 256, spring 258, spacer 262, knob 264, and/or spacer 266. (FIGS. 19-20). Cable assembly 238A may be configured to increase traction. Cable assembly 238B may be configured to reduce or release traction. Trigger 252 may be configured to actuate cable assembly 238A, thereby moving plate assembly 211 to increase traction. As discussed with respect to handle assembly 102, spacer 248, balls 250, and trigger 252 of handle assembly 202 may be configured to compress spring 258 thereby causing balls 250 to skip to the next slot of spacer 248 when a traction limit set by knob 264 is met. To retract plate assembly 110 and/or release traction, release 249 may be configured to urge cable assembly 238B to disengage stop pawn 296 and drive pawn 298 from plate 272 thereby reducing and/or releasing traction applied by plate assembly 110. Handle assembly 202 may include or be used in conjunction with any embodiment disclosed herein.

Drive assembly 206 may include retractor 270, retractor spring 271, plate 272, spring 274A, spring 274B, spring 274C, spring 274D, angle button 283, angle pin 285, angle arm 286, base arm 288A, base arm 288B, base arm 289, stop pawn 296, and/or drive pawn 298. (FIGS. 21-24). As mentioned above, traction system 200 may include multiple cables configured to independently increase and/or decrease traction. Cable assembly 238A may be configured to increase traction and cable assembly 238B may be configured to reduce or release traction. Cable assembly 238A may be connected to drive pawn 298 to thereby ratchet drive pawn 298 along plate 282. Stop pawn 296 may be configured to hold plate 282 for the ratcheting of drive pawn 298. Cable assembly 238B may be configured to disconnect stop pawn 296 and drive pawn 298 from plate 272, for example, to reduce or release traction. With actuation of trigger 252, the teeth of drive pawn 298 may be pulled out of the slots of plate 272 and advance into the next set of slots in plate 272 while stop pawn 296 resists movement of plate 272 with respect to housing assembly 211. As the trigger 252 is reset, drive pawn 298 may articulate back to re-engage a further slot of plate 272 with a force from spring 274. Stop pawn 296 may substantially maintain a distraction force or distance on the user while drive pawn 298 articulates across plate 272. After release 249 handle assembly 206 is actuated to release traction, refractor spring 271, for example a constant force spring, may return plate 272 to a retracted condition, for example toward retractor 270.

Figure 27:
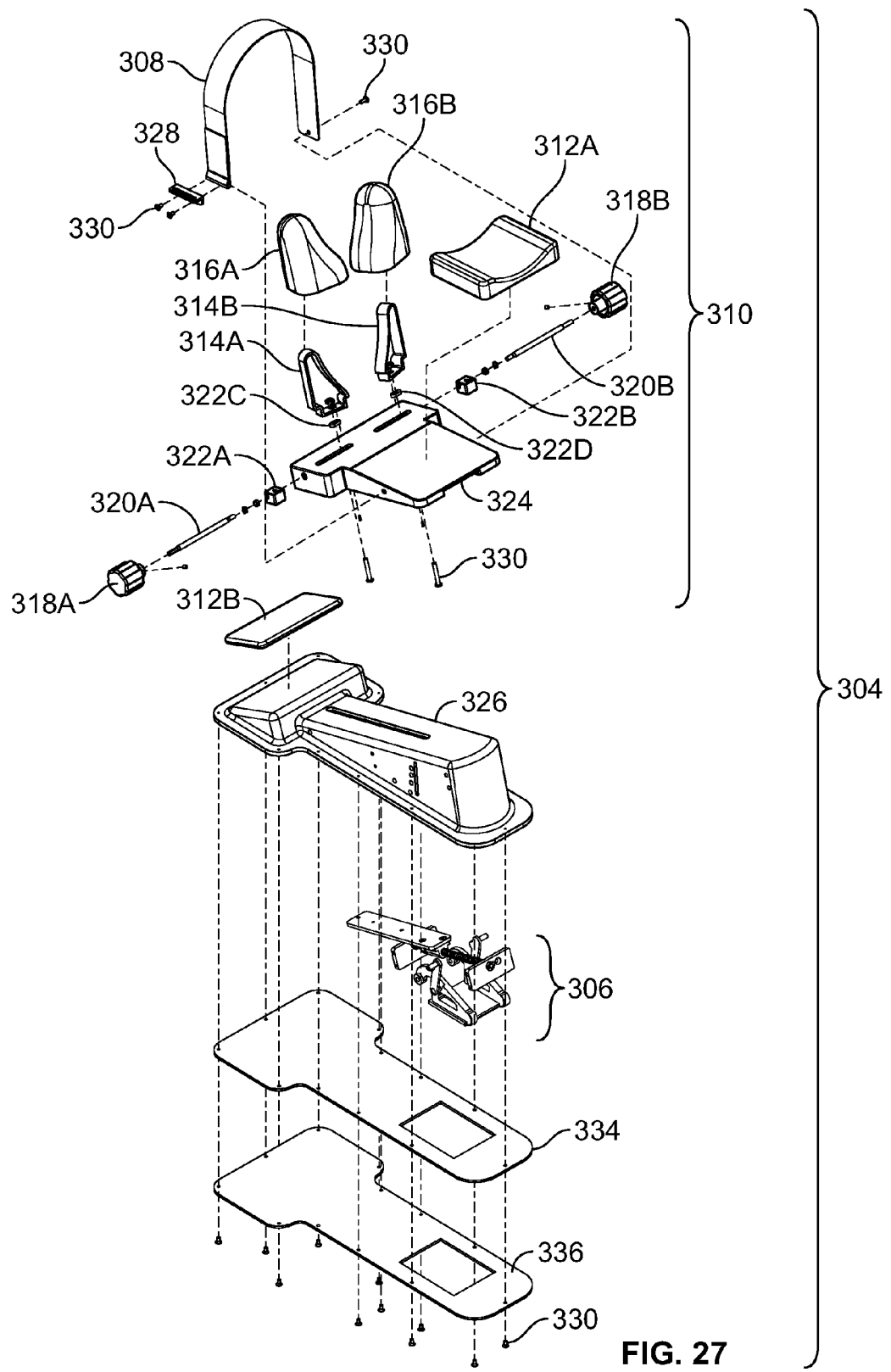
FIG. 27 illustrates an exploded view of an embodiment of FIG. 25.

Referring to FIGS. 25-31, traction system 300 may include handle assembly 302, cable assembly 338, and/or traction assembly 304. Any portion of traction system 300 may include the same or similar components as any of the alternative embodiments disclosed herein including the accompanying drawings. Traction assembly 304 may include plate assembly 310 and housing assembly 311. (FIG. 27). Plate assembly 310 may include strap 308, pad 312A, inserts 314A-B, supports 316A-B, knob 318A-B, rod 320A-B, block 322A-D, plate 324, and/or fasteners 330. (FIG. 27). Housing assembly 311 may include drive assembly 306, pad 312B, housing 326, fasteners 330, cover 334, and/or bottom 336.

Figure 28:
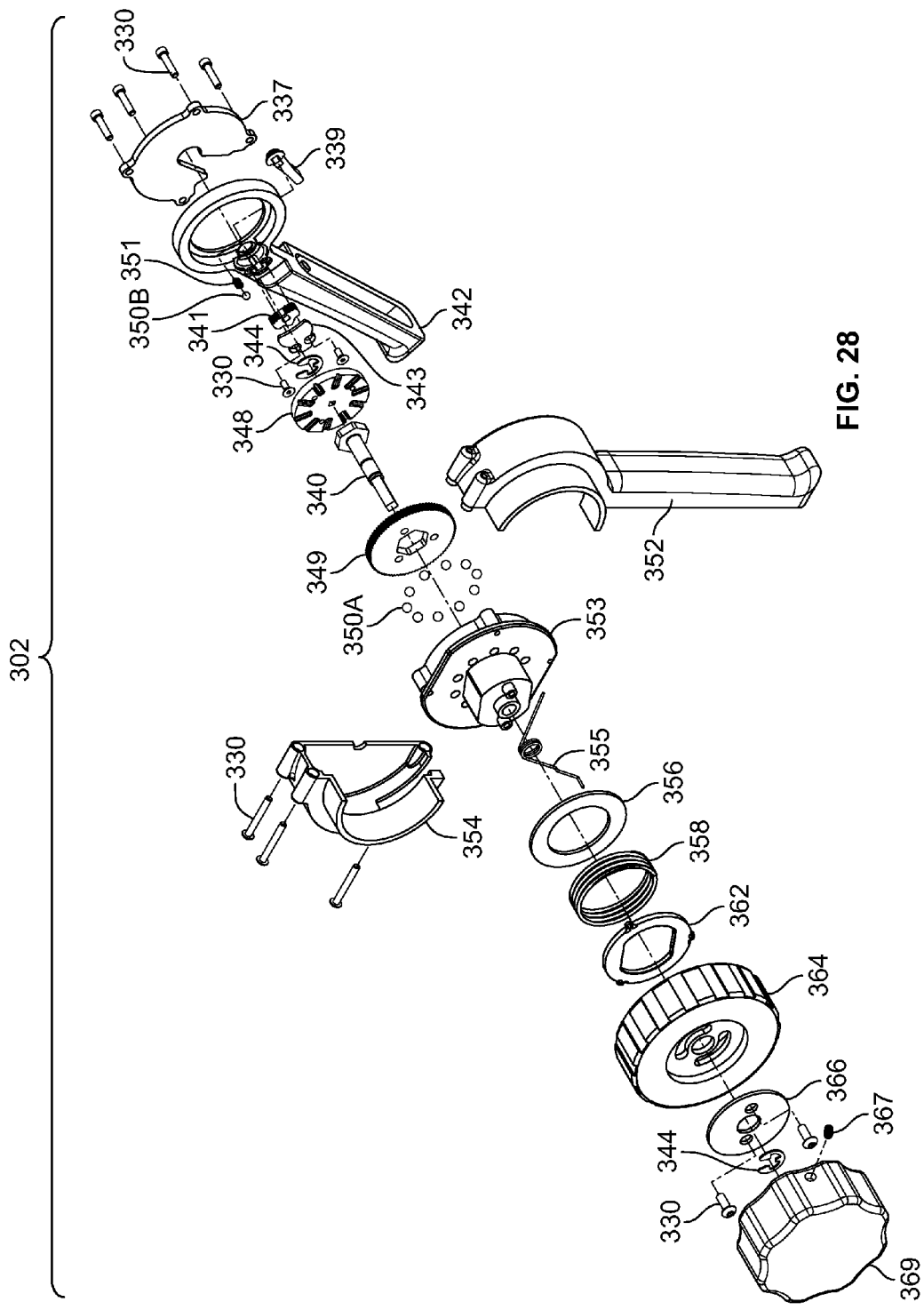
FIG. 28 illustrates an exploded view of an embodiment, for example, an alternative handle assembly.
Figure 29:
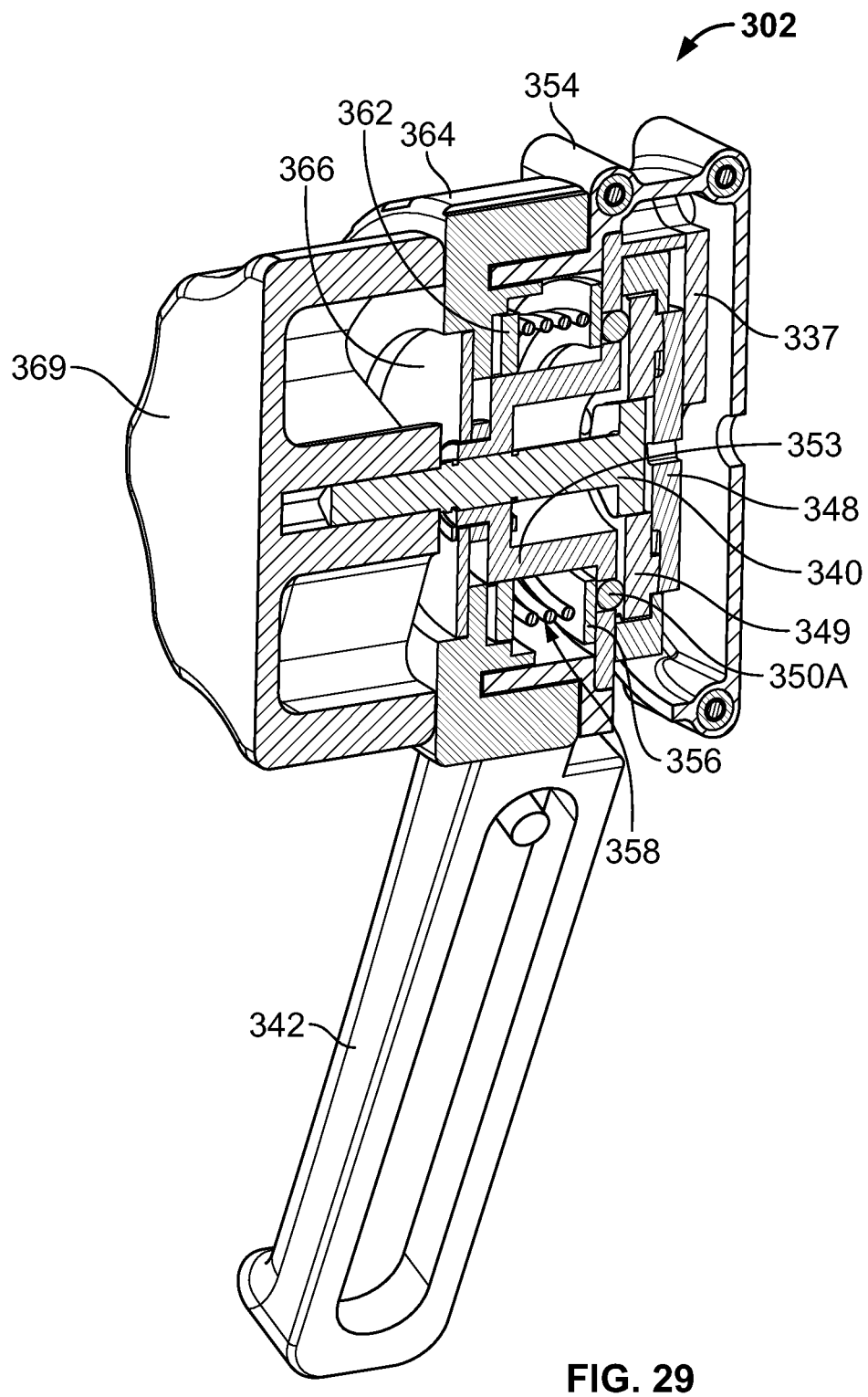
FIG. 29 illustrates a section view of an embodiment of FIG. 28.

Handle assembly 302 may include fasteners 330, spacer 337, member 339, pawn 341, trigger 342, spacer 348, insert 340, clips 344, gear 349, balls 350A, ball 350B, spring 351, spacer 353, housing 352, housing 354, spring 355, spacer 356, spring 358, spacer 362, knob 364, spacer 366, screw 367, and knob 369. (FIG. 28-29). Knob 364 may be configured to set the traction limit. Trigger 342 and knob 369 may be configured to rotate the cable of cable assembly 338 to move plate assembly 310 along housing assembly 311 thereby increasing or decreasing traction. In an embodiment, knob 369 may be configured to apply course or greater movement of plate assembly 310 and trigger 342 may be configured to apply fine or less movement of plate assembly 310. Alternatively, trigger 342 and knob 369 may have an opposite configuration. Pawn 341 may be configured to releasably engage gear 349. When trigger 342 is actuated (i.e. squeezed), pawn 341 may be engaged into the teeth of gear 349 with pressure from spring 351 and ball 350B, thereby rotating and/or actuating gear assembly 338. When trigger 342 is released, pawn 341 may disengage the teeth on gear 349 by rotating and depressing spring 351 and ball 350B. Lever 339 is used to disengage trigger 342 while the knob 369 is used to release traction. Handle assembly 302 may include or be used in conjunction with any embodiment disclosed herein.

Figure 30:
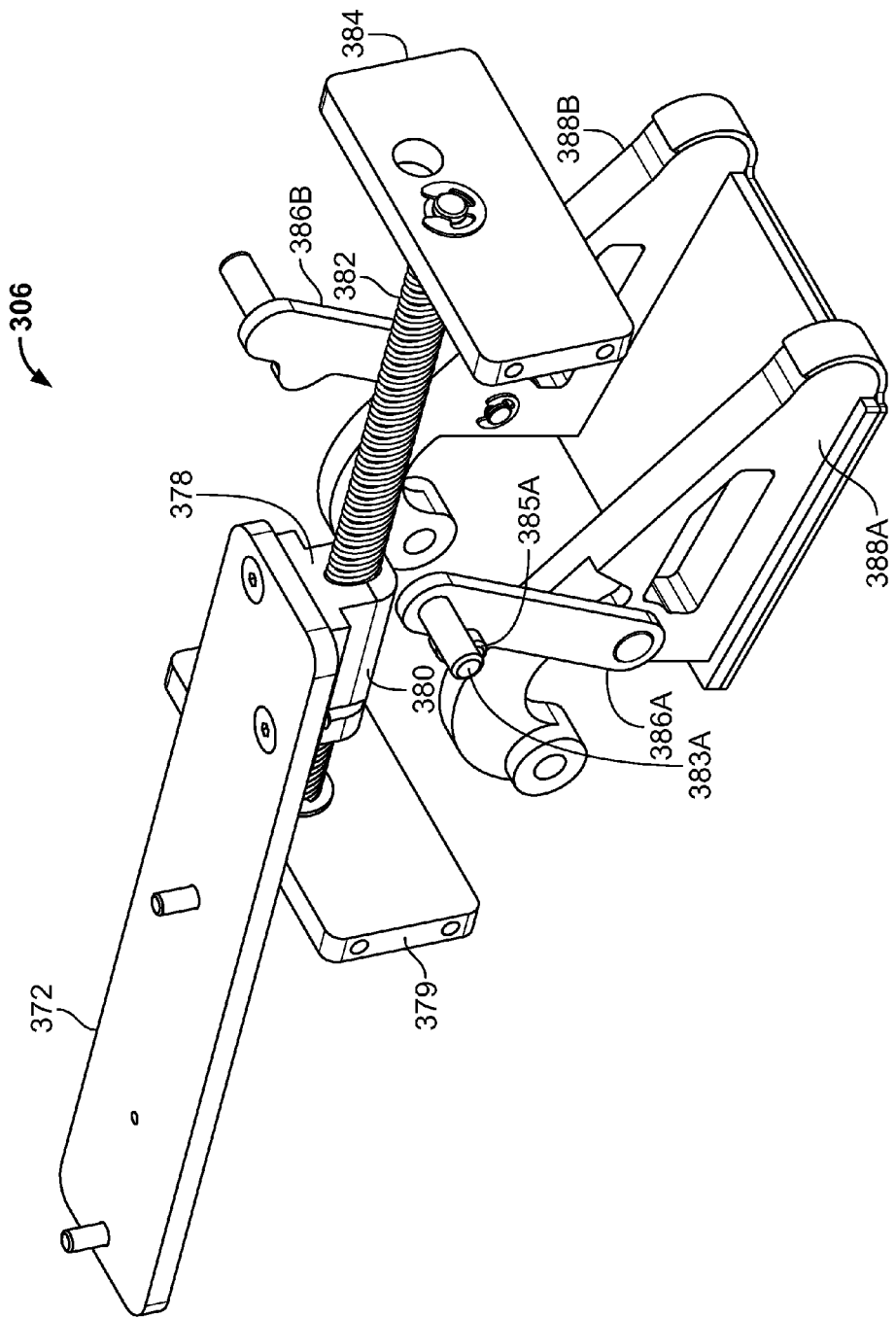
FIG. 30 illustrates an isometric view of an embodiment, for example an alternative drive assembly.
Figure 31:
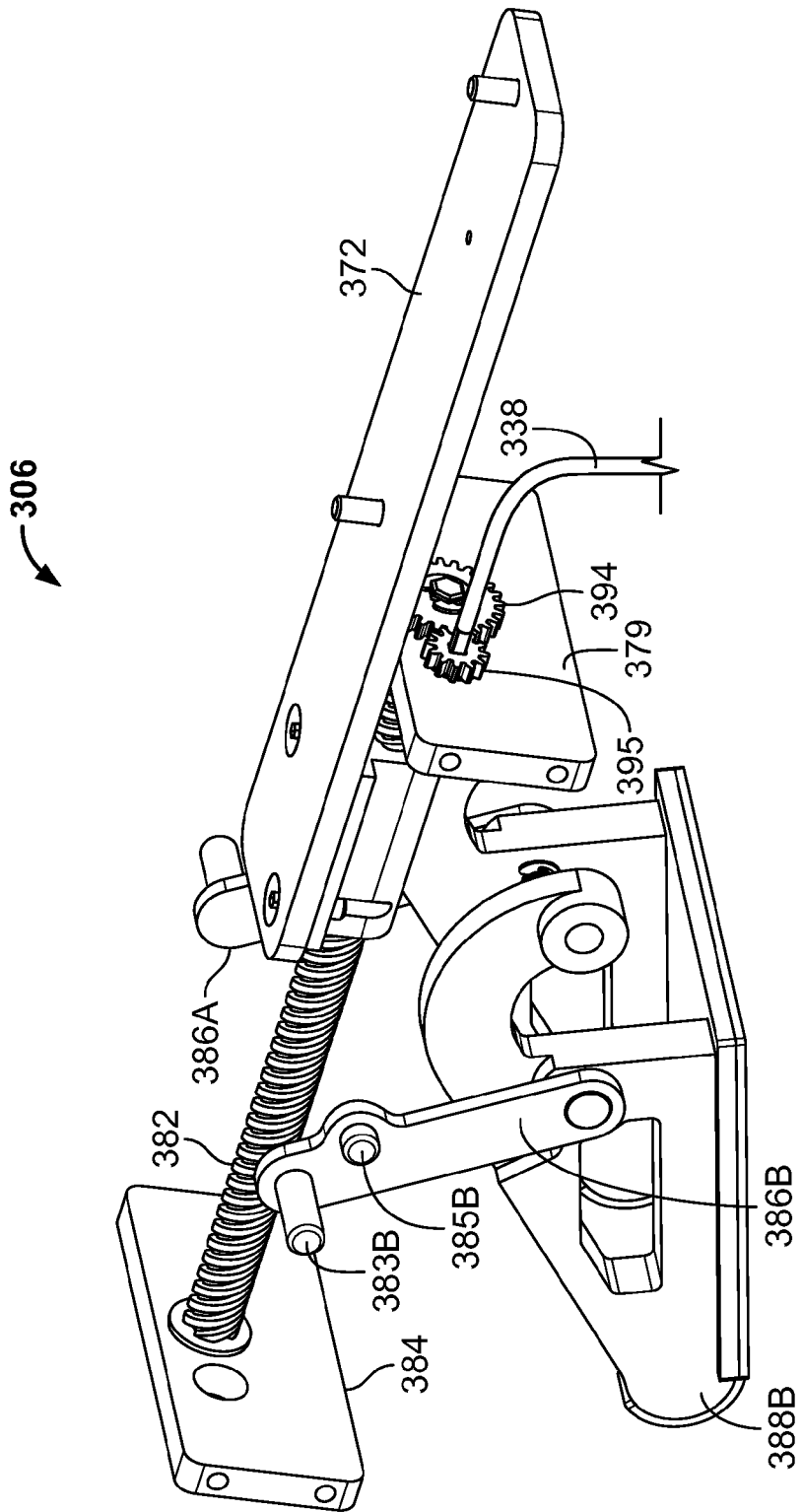
FIG. 31 illustrates an opposite isometric view of FIG. 30.

Drive assembly 306 may include plate 372, upper member 378, lower member 380, lead screw 382, angle buttons 383A-B, angle pins 385A-B, angle arms 386A-B, base arms 388A-B, gear 394, and gear 395. (FIGS. 30-31). Traction system 300 may include cable assembly 338 with a cable rotationally connected to gear 395. Gear 395 may engage gear 394 connected to lead screw 382. The cable may include a flexible cable. Actuation of trigger 348 may rotate the cable of cable assembly 338 to directly rotate gear 395. Gear 395 may rotate gear 394, which then directly rotates lead screw 382. All or any portion of upper member 378 and/or lower member 380 may be threaded to engage lead screw 382. Lead screw 382 may be configured to advance plate 372, which is connected to plate assembly 310. As such, actuation of trigger 342 or knob 369 may advance plate assembly 310 in either direction along housing assembly 311 to provide or reduce traction.

Figure 34:
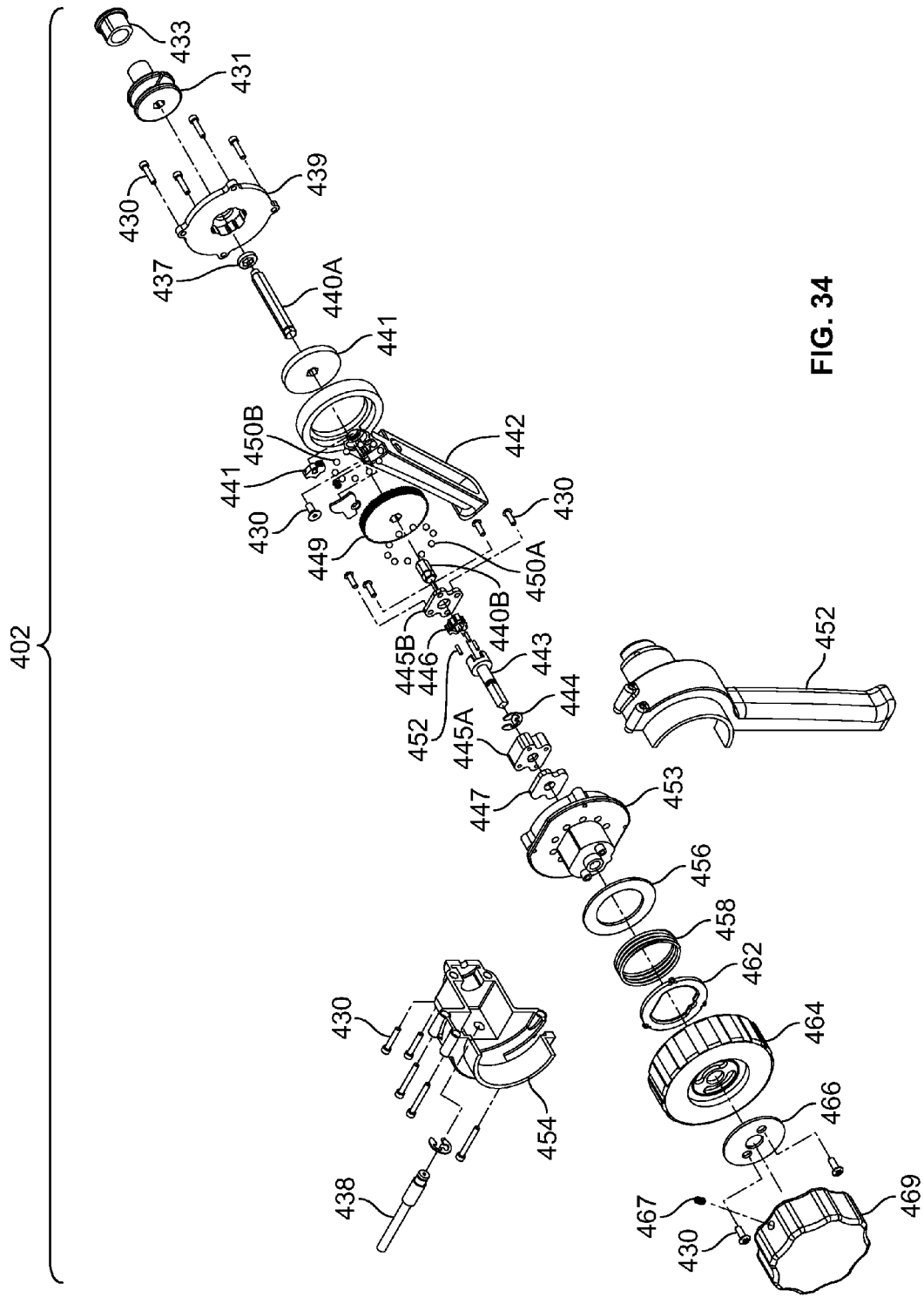
FIG. 34 illustrates an exploded view of an embodiment of FIG. 32.

With reference to FIGS. 32-34, handle assembly 402 may include cap 433, spool 431, fasteners 430, spacer 439, spacer 437, insert 440A, trigger 442, pawn 441, gear 449, balls 450A, balls 450B, spacer 445A, spacer 445B, spacer 446, pins 452, insert 443, clip 444, spacer 447, housing 452, spacer 453, housing 454, spacer 456, spring 458, spacer 462, knob 464, and/or spacer 466. (FIGS. 32-34) Spool 431 may be configured to rotationally receive and wrap the cable of cable assembly 438, for example, to advance the cable. Handle assembly 402 may also be configured with anti-reversing features. Spacer 446 may allow rotation of pins 452 to advance the cable, but pins 452 may lock into spacer 446 to stop rotation in the reverse direction. As such, the cable may advance plate assembly 410 with respect to housing assembly 411, but the anti-reversing features may stop the cable from reversing into handle assembly 402 and/or reduce cable slack on spool 431. Handle assembly 402 may include or be used in conjunction with any embodiment disclosed herein.

Figures 35, 36:
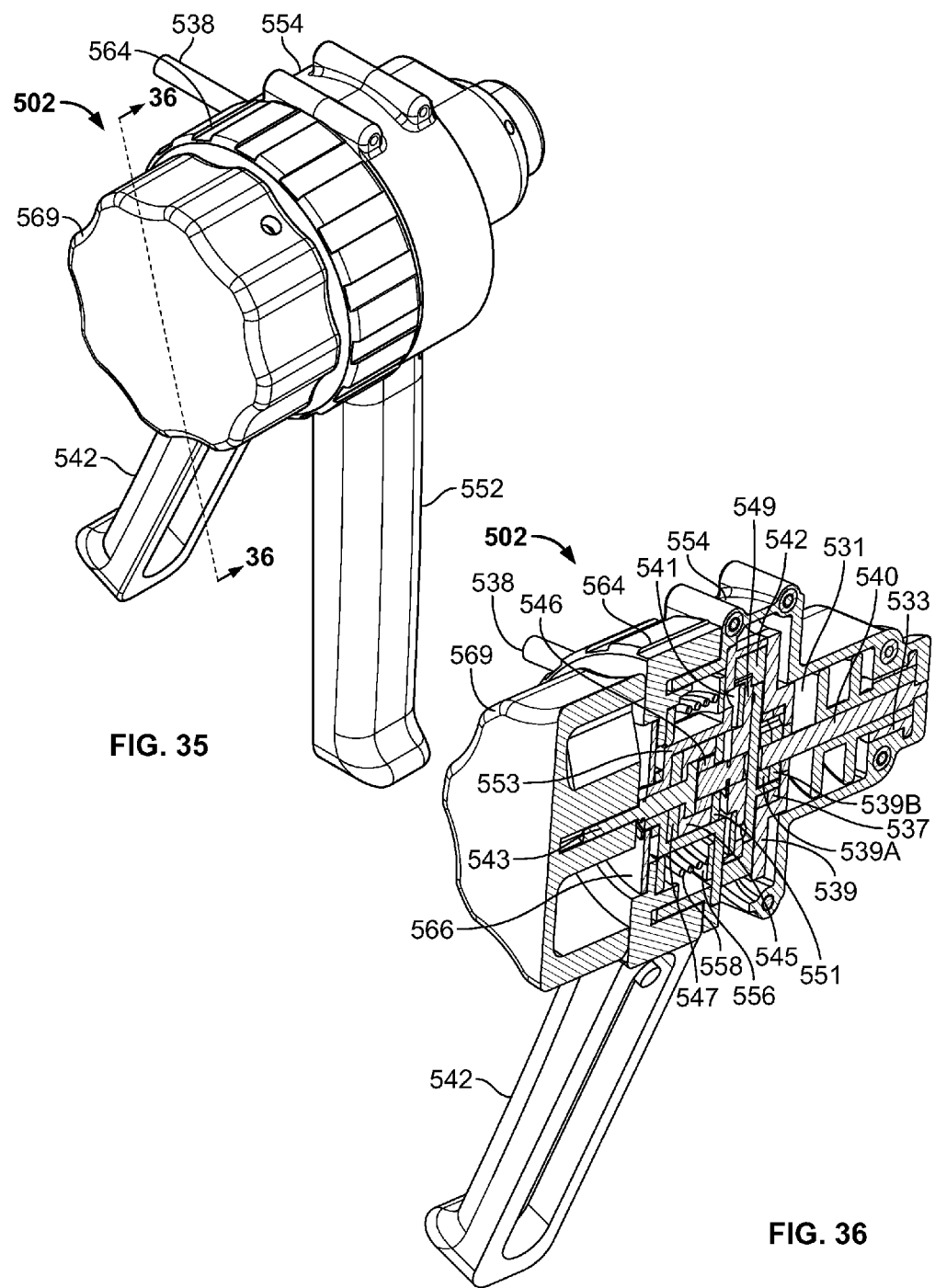
FIG. 35 illustrates an isometric view of an embodiment, for example an alternative handle assembly.
FIG. 36 illustrates a section view of an embodiment of FIG. 35.
Figure 37:
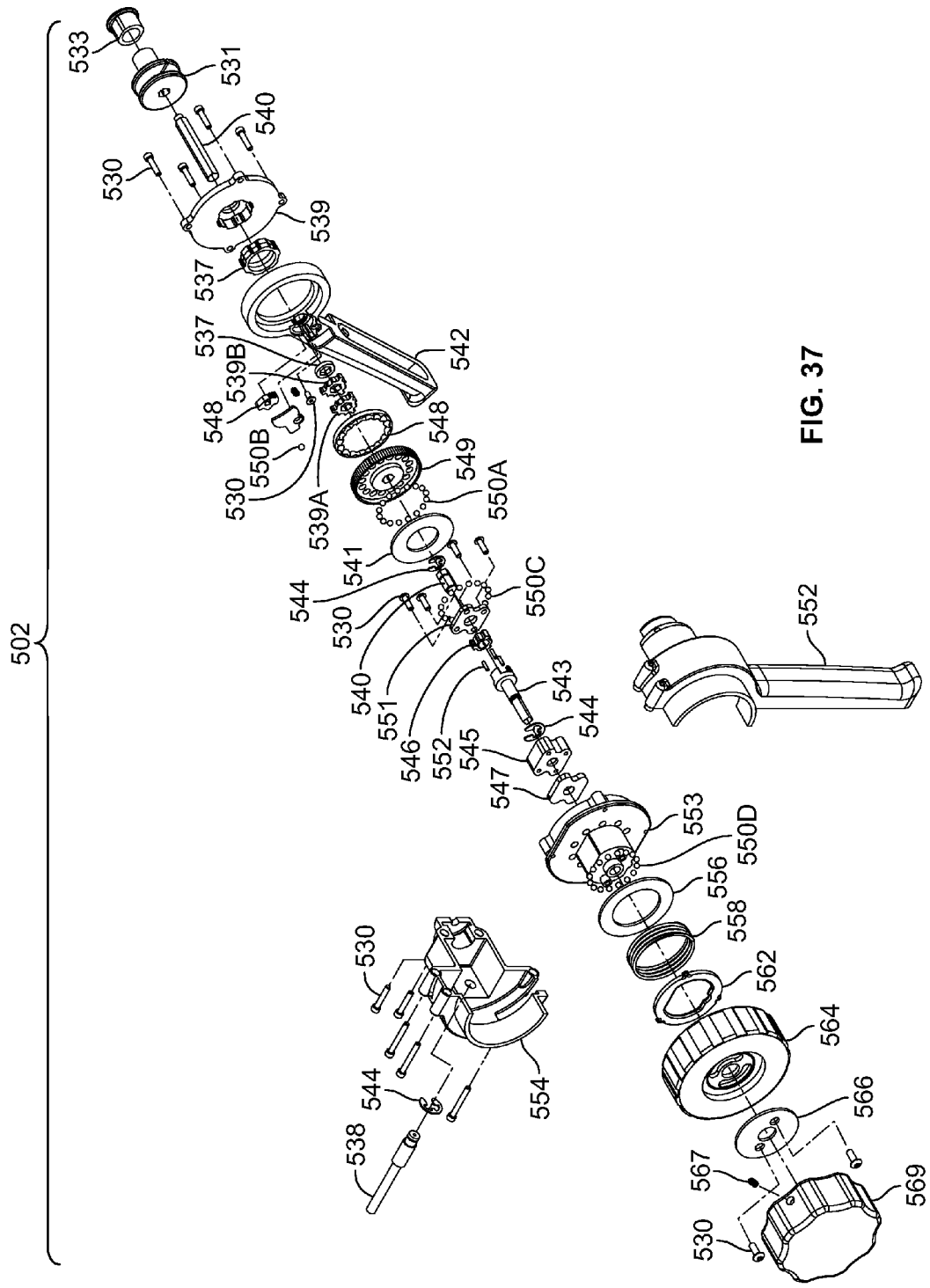
FIG. 37 illustrates an exploded view of an embodiment of FIG. 35.

Referring to FIGS. 35-37, handle assembly 502 may include cap 533, spool 531, insert 540, fasteners 530, spacer 539, spacer 537, pawn 548, spacer 539A, spacer 539B, spacer 548, gear 549, balls 550A, ball 550B, balls 550C, balls 550D, spacer 541, clips 544, insert 540, spacer 551, insert 546, pin 552, insert 543, spacer 545, spacer 547, housing 552, housing 554, spacer 553, spacer 556, spring 558, spacer 562, knob 564, spacer 566, and/or knob 563. Handle assembly 502 may include or be used in conjunction with any embodiment disclosed herein.

Figure 40:
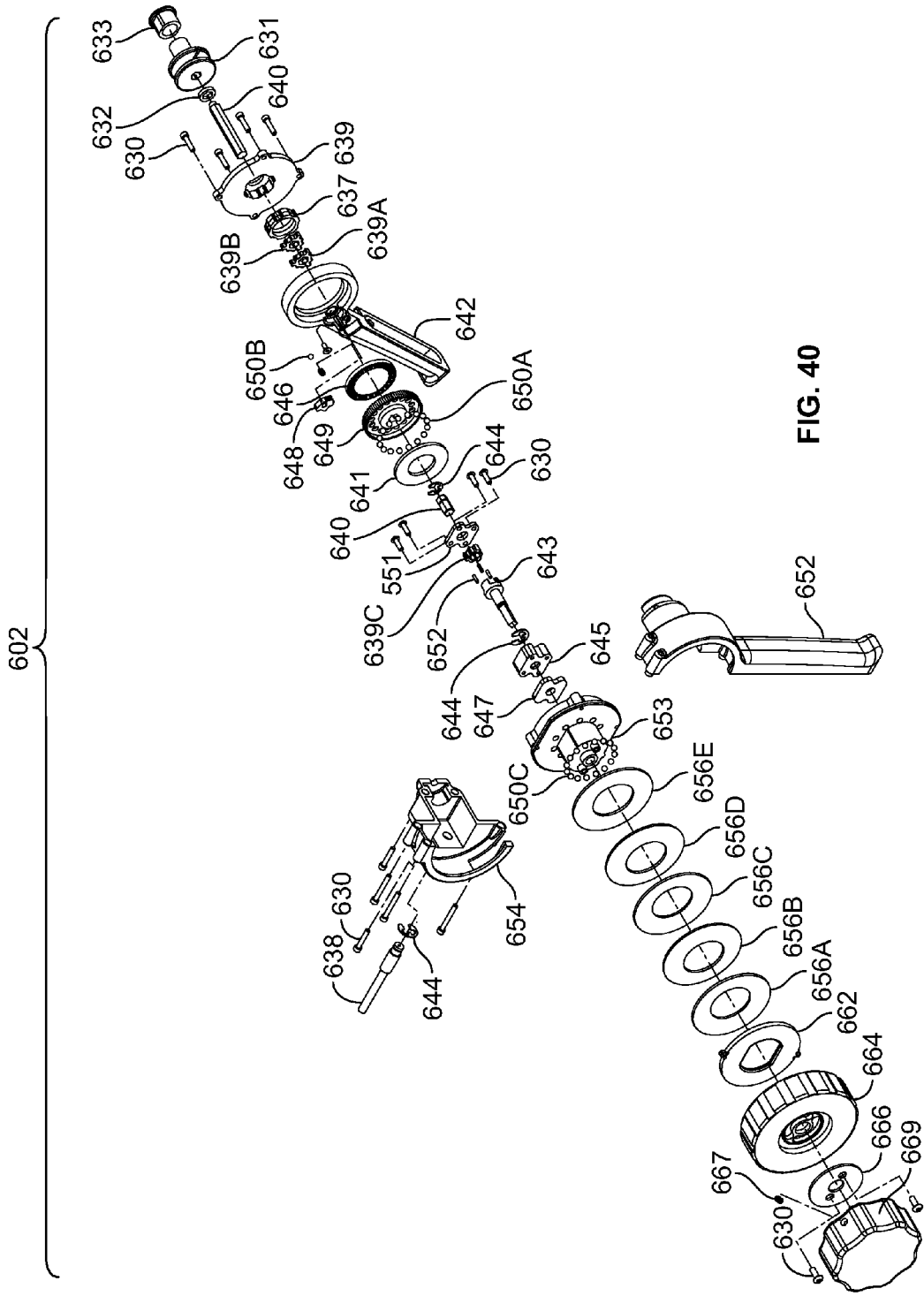
FIG. 40 illustrates an exploded view of an embodiment of FIG. 38.
Figure 41:
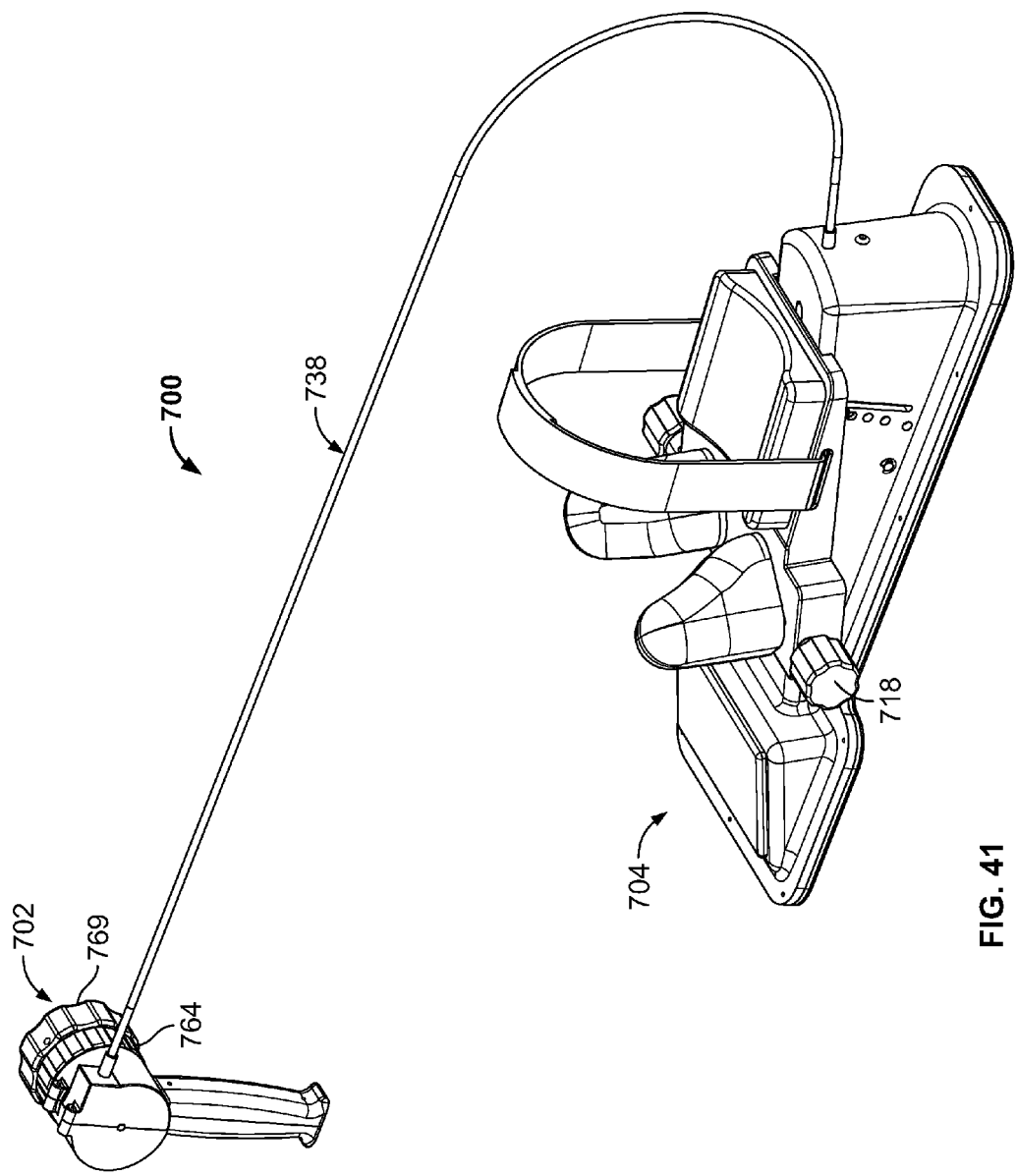
FIG. 41 illustrates an isometric view of an embodiment, for example an alternative traction system.

With reference to FIGS. 38-40, handle assembly 602 that may include cap 633, spool 631, spacer 632, fasteners 630, spacer 639, spacer 639A, spacer 639B, trigger 642, ball 650A, balls 650B, balls 650C, spacer 646, pawn 648, gear 649, spacer 641, clips 644, insert 640, spacer 639C, pins 652, insert 643, spacer 645, spacer 647, spacer 653, springs 656A-E, spacer 662, knob 664, spacer 666, and/or knob 669. Handle assembly 602 may include or be used in conjunction with any embodiment disclosed herein.

Figure 42:
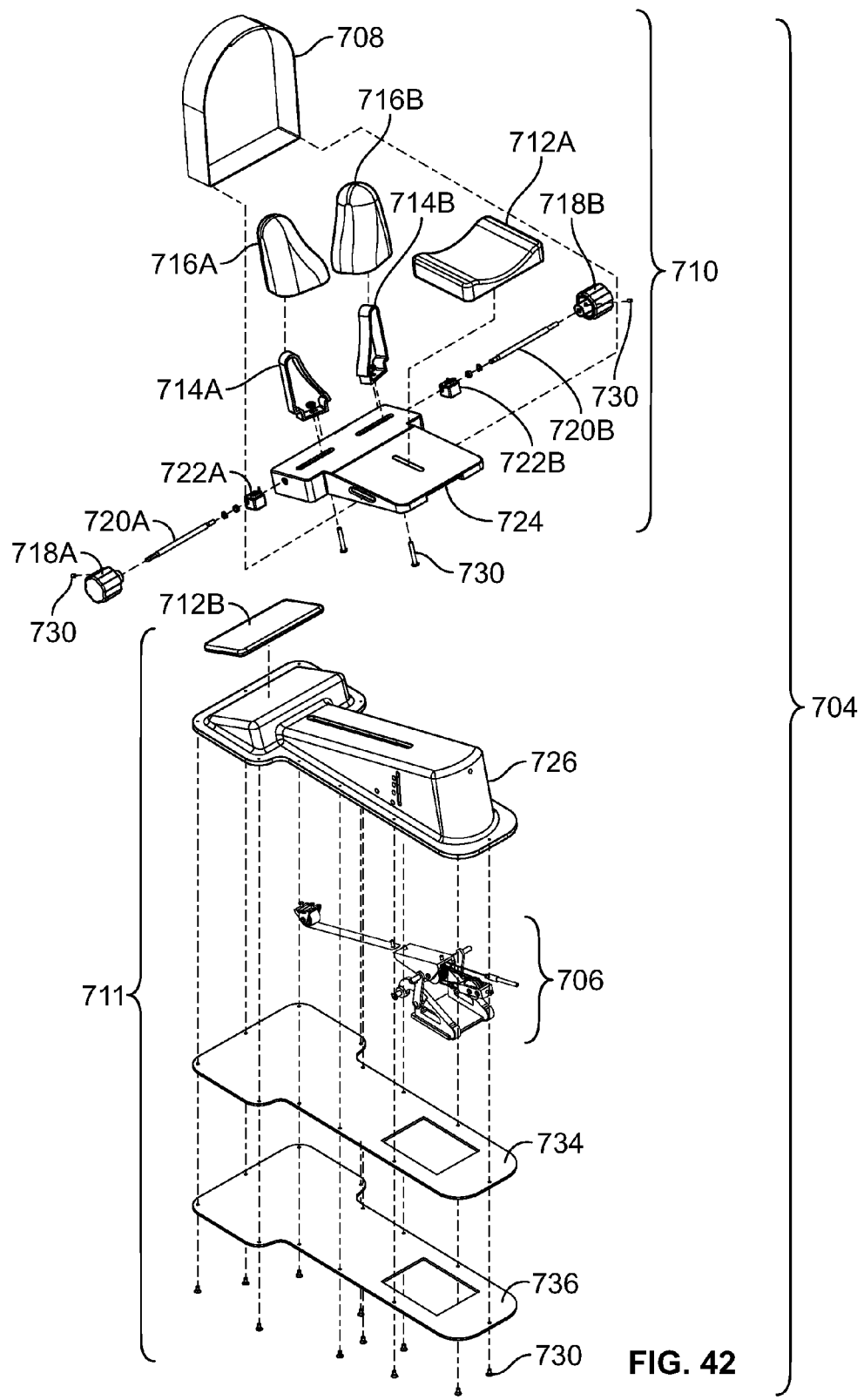
FIG. 42 illustrates an exploded view of the embodiment of FIG. 41.

Referring to FIGS. 41-45, traction system 700 may include handle assembly 702, cable assembly 738, and traction assembly 704. Any portion of traction system 700 may include the same or similar components as any of the alternative embodiments disclosed herein including the accompanying drawings. Traction assembly 704 may include plate assembly 710 and housing assembly 711. (FIG. 42). Plate assembly 710 may include strap 708, pad 712A, inserts 714A-B, supports 716A-B, knobs 718A-B, rods 720A-B, blocks 722A-B, plates 724, and/or fasteners 730. (FIG. 42). Housing assembly 711 may include drive assembly 706, pad 712B, housing 726, fasteners 730, cover 734, and/or bottom 736.

Figure 43:
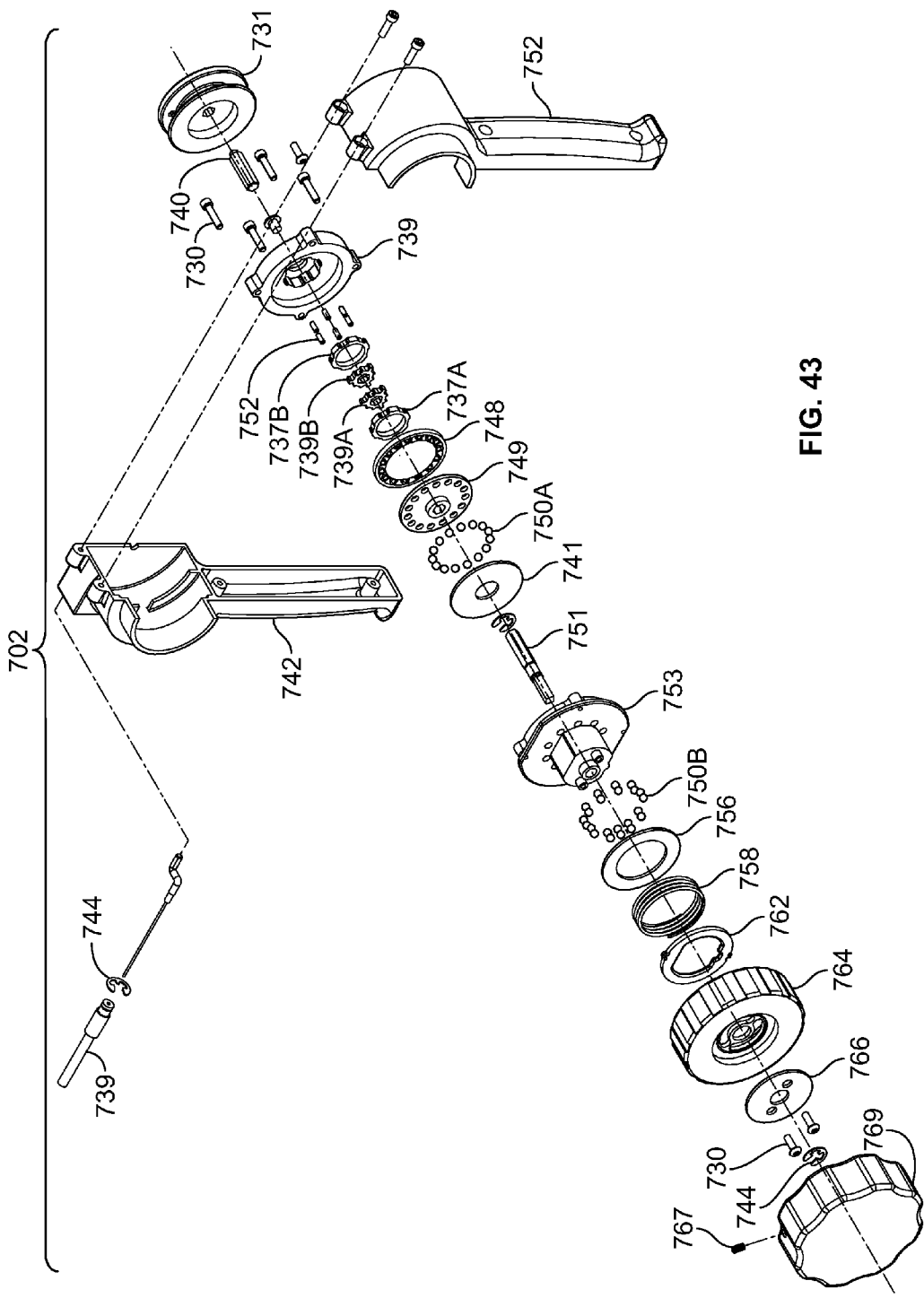
FIG. 43 illustrates an exploded view of an embodiment, for example an alternative handle assembly.
Figure 44:
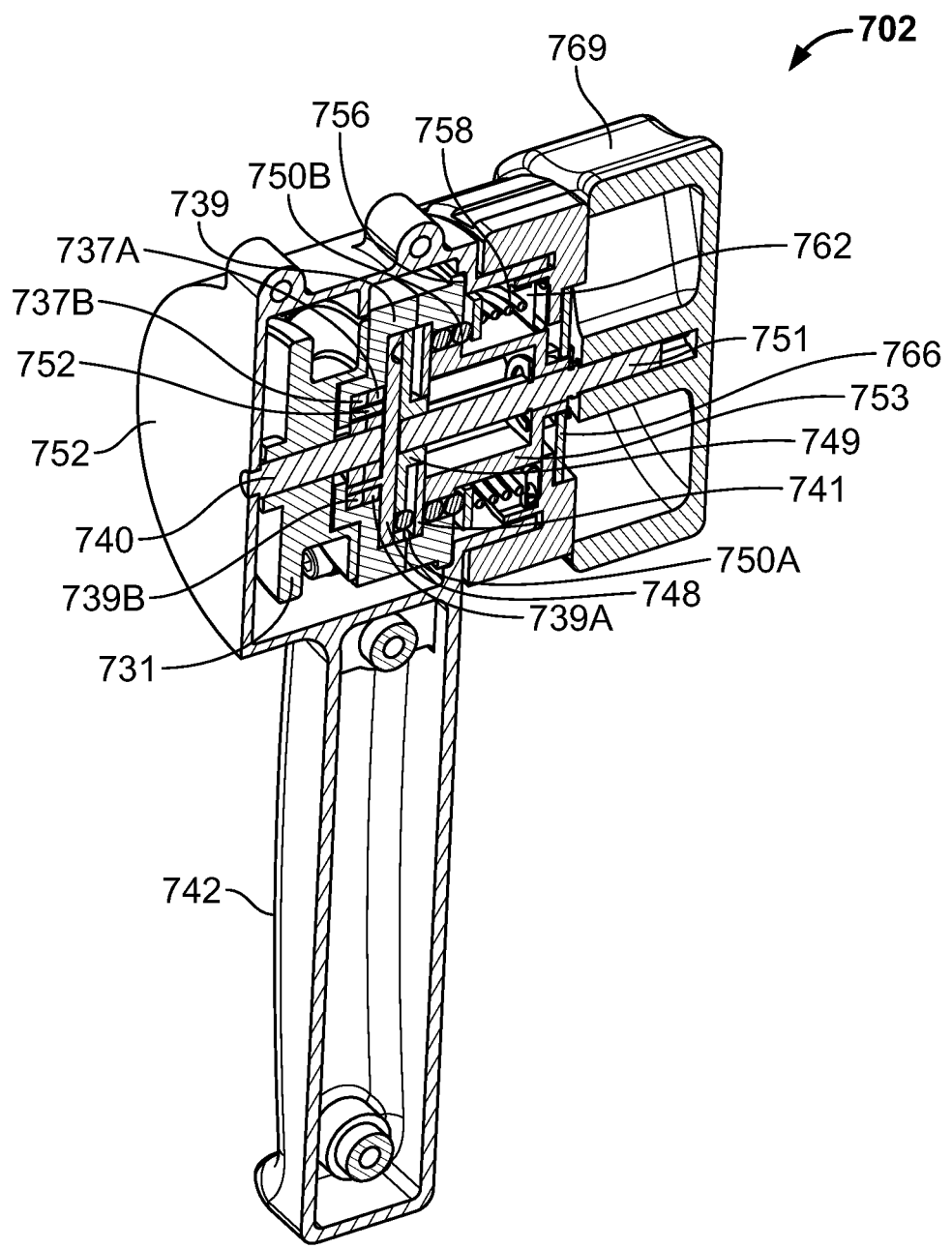
FIG. 44 illustrates a section view of an embodiment of FIG. 43.

Handle assembly 702 may include spool 731, insert 740, fasteners 730, spacer 739, pins 752, spacer 737A, spacer 737B, spacer 739A, spacer 739B, spacer 748, spacer 749, balls 750A, balls 750B, spacer 741, insert 751, insert 753, spacer 756, spring 758, spacer 762, knob 764, spacer 766, screw 767, and/or knob 769. (FIG. 43). Spool 731 may be configured to receive and wrap the cable of cable assembly 738. Knob 764 may set the traction limit. Knob 769 may increase or decrease tension on the cable 782 of cable assembly 738. Handle assembly 702 may include or be used in conjunction with any embodiment disclosed herein.

Figure 45:
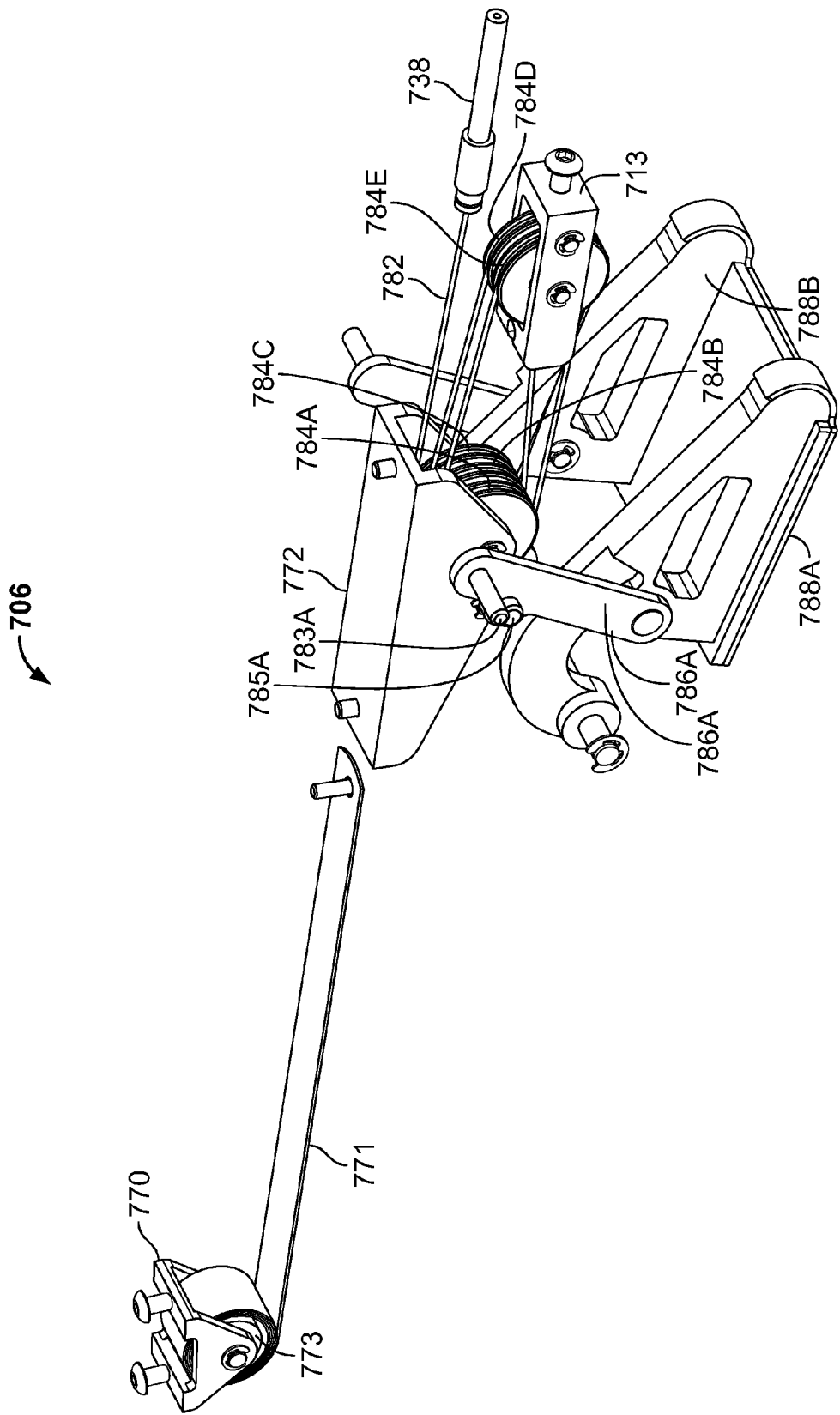
FIG. 45 illustrates an isometric view of an embodiment, for example an alternative drive assembly.
Figure 46:
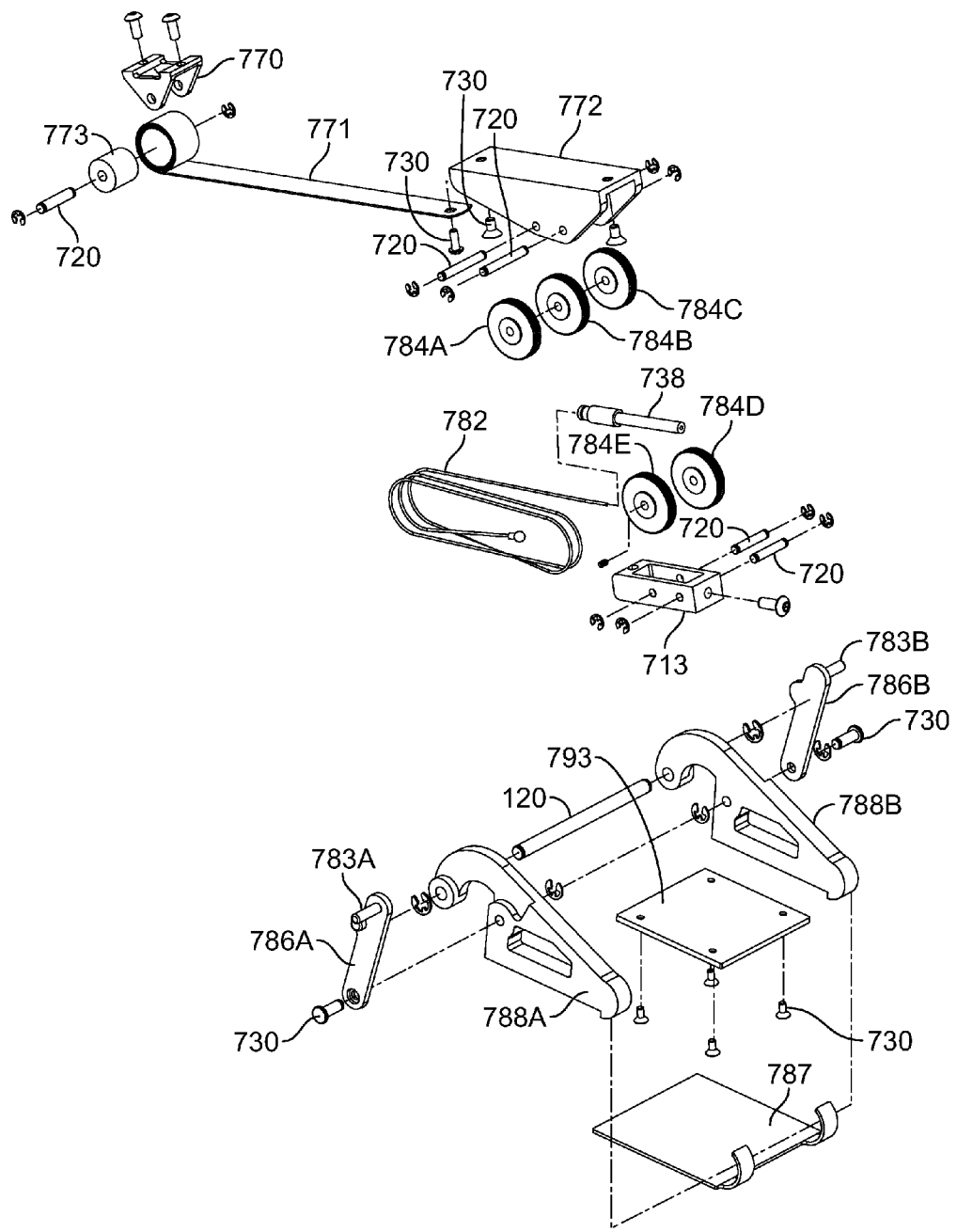
FIG. 46 illustrates an exploded view of an embodiment of FIG. 45.

Drive assembly 706 may include pulley head 713, retractor 770, retractor spring 771, plate 772, spool 773, angle button 783, pulleys 784A-E, angle pin 785, angle arm 786, base arm 788A, and base arm 788B. (FIGS. 45-46). Cable 782 may be wound around pulleys 784A-E and secured to pulley head 713. Tension on cable 782 of cable assembly 738 may urge pulleys 784-C toward pulleys 784D-E. The ratio of the size (i.e. diameter) of pulleys 784A-E with respect to each other may be configured to increase or decrease the ratio of distraction distance or force applied by plate 772 relative to the change in length or force on cable 782. Rotation of knob 767 may increase or decrease tension on cable 782 to urge plate 772 respectively toward or away from pulley head 713 connected to housing 726. Retractor 770 may also urge plate 772 toward a retracted condition with retractor spring 771, for example a constant force spring. Movement of plate 772 toward pulley head 713 may advance plate assembly 710 along housing assembly 711 to increase traction. Movement of plate 772 toward retractor 770 may retract plate assembly 710 to reduce or release traction. Tension applied by cable 782 may control the distraction distance and/or force applied by plate 772 to plate assembly 710. Thus, the change in length and/or force applied by cable 782 may translate directly into a distraction distance or force on the cervical spine.

Additional embodiments may include or be used in conjunction with devices and methods disclosed in U.S. Pat. No. 7,182,738, titled "Patient Monitoring Apparatus and Method for Orthosis and Other Devices" and U.S. Pat. No. 8,251,934, titled "Orthosis and Method for Cervical Mobilization", which are hereby incorporated by referenced in their entirety.

The embodiments herein may be manufactured with any material or process suitable for medical use or to provide traction or distraction to a portion of a body. For example, embodiments may include any metal, polymer, or elastic material. Polymers may include polycarbonate, polyethylene, acrylonitrile butadiene styrene (ABS), delrin, or lexan. Metals may include steel, stainless steel, or aluminum. Elastic materials may include rubber, silicone, or foam. Embodiments may be vacuum formed, injection molded, machined, or waterjet cut. Embodiments may also include any combination of these materials and/or processes.

All or any portion of any embodiment herein may include any combination of the embodiments disclosed herein. As used herein, an element or act recited in the singular and proceeded with the word "a" or "an" should be understood as not excluding plural elements or acts unless such exclusion is explicitly recited. Furthermore, references to "embodiment" or "embodiments" of the present disclosure are not intended to be interpreted as excluding the existence of additional embodiments. Moreover, reference numbers including letters are intended to provide example locations with respect to the drawings but are not intended to be interpreted as limiting their interchangeability with any embodiments herein.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A cervical traction system for a neck of a user, the system comprising:
   a plate assembly including first and second supports configured to engage a portion of a head of the user, and first and second transverse drive members configured to move the respective first and second supports to adjust a transverse distance between the first and second supports;
   a housing assembly including a longitudinal drive member configured to move the plate assembly relative to the housing assembly; and
   a handle assembly operatively connected to the longitudinal drive member,
   wherein movement of the plate assembly is configured to urge the first and second supports against the head to apply traction to the neck, and
   wherein the longitudinal drive member and plate assembly are releasably connected and selectively releasable to allow sliding movement of the plate assembly along a length of the longitudinal drive member to adjust a position of the plate assembly relative to the housing, the sliding movement of the plate assembly being limited by the longitudinal drive member when the plate assembly and longitudinal drive member are connected.

2. The system of claim 1, the plate assembly includes first and second knobs operative to actuate the respective first and second transverse drive members to adjust the first and second supports.

3. The system of claim 1, wherein the handle assembly comprises a trigger configured to actuate the longitudinal drive member.

4. The system of claim 1, wherein the handle assembly comprises a knob configured to actuate the longitudinal drive member.

5. The system of claim 1, wherein the longitudinal drive member includes a worm gear or pulley.

6. The system of claim 1, wherein the longitudinal drive member is non-pneumatic.

7. The system of claim 1, wherein movement of the plate assembly is configured to apply traction to a portion of the cervical spine.

8. A cervical traction system for a neck of a user, the system comprising:
   a housing assembly including a drive assembly;
   a plate assembly operatively connected to the drive assembly and comprising at least one support configured to engage a portion of a head of the user, wherein the drive assembly is configured to drive movement of the plate assembly relative to the housing assembly;
   a cable assembly operatively connected to the drive assembly, wherein the cable assembly is configured to drive movement of the drive assembly;
   a handle assembly operatively connected to the cable assembly, wherein the handle assembly is configured to actuate movement of the cable assembly to drive movement of the drive assembly, which in turn drives movement of the plate assembly relative to the housing assembly, wherein movement of the plate assembly is configured to apply traction to the neck; and
   a clutch operatively connected between the handle assembly and the plate assembly to prevent actuation of the handle assembly from causing driven movement of the plate assembly when the amount of traction applied to the neck exceeds a traction limit.

9. The system of claim 8, wherein the at least one support includes a first support and a second support, the system further comprising a transverse drive member configured to adjust a transverse distance between the first and second supports.

10. The system of claim 8, wherein the handle assembly comprises a trigger configured to actuate movement of the cable assembly.

11. The system of claim 8, wherein the handle assembly comprises a knob configured to actuate movement of the cable assembly.

12. The system of claim 8, wherein the drive assembly includes a worm gear or pulley.

13. The system of claim 8, wherein the drive assembly is non-pneumatic.

14. The system of claim 8, wherein movement of the plate assembly is configured to apply traction to a portion of the cervical spine.

15. A method of using a cervical traction device for a neck of a patient, the method comprising:
   providing the cervical traction device including a housing assembly having a longitudinal drive, a plate assembly including at least one support configured to engage a portion of a head of the patient, a cable assembly operatively connected to the longitudinal drive, a handle assembly operatively connected to the cable assembly, and a clutch assembly operatively connected between the handle assembly and the plate assembly;
   positioning a neck of the patient with respect to the plate assembly and the at least one support;
   actuating a traction knob or a trigger of the handle assembly to actuate movement of the cable assembly to drive movement of the longitudinal drive, which in turn drives movement of the longitudinal drive to move the plate assembly relative to the housing assembly to provide a traction force to at least a portion of the neck; and
   using the clutch to prevent actuation of the handle assembly from causing driven movement of the plate assembly when the amount of traction applied to the neck exceeds a traction limit.

16. The method of claim 15, further comprising rotating a limit knob to adjust the traction limit.

17. The method of claim 15, further comprising rotating a support knob of the housing assembly to adjust a transverse distance between first and second supports of the at least one support to engage at least a portion of the neck.

18. The method of claim 15, wherein the longitudinal drive includes a worm gear or pulley.

19. The method of claim 15, wherein the longitudinal drive is non-pneumatic.

20. The method of claim 15, wherein movement of the plate assembly is configured to apply traction to a portion of the cervical spine.

* * * * *